United States Patent
Nishio

(10) Patent No.: US 11,076,750 B2
(45) Date of Patent: Aug. 3, 2021

(54) IMAGING SYSTEM AND ENDOSCOPE SYSTEM

(71) Applicant: OLYMPUS CORPORATION, Tokyo (JP)

(72) Inventor: Masahiro Nishio, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 617 days.

(21) Appl. No.: 15/876,392

(22) Filed: Jan. 22, 2018

(65) Prior Publication Data

US 2018/0140173 A1    May 24, 2018

Related U.S. Application Data

(63) Continuation of application No. PCT/JP2015/070920, filed on Jul. 23, 2015.

(51) Int. Cl.
*A61B 1/00* (2006.01)
*A61B 1/06* (2006.01)
(Continued)

(52) U.S. Cl.
CPC ............ *A61B 1/06* (2013.01); *A61B 1/00006* (2013.01); *A61B 1/00009* (2013.01); *A61B 1/043* (2013.01); *A61B 1/045* (2013.01); *A61B 1/05* (2013.01); *A61B 1/0653* (2013.01); *A61B 1/0669* (2013.01); *A61B 1/07* (2013.01); *G02B 23/2484* (2013.01); *H04N 5/2256* (2013.01);
(Continued)

(58) Field of Classification Search
None
See application file for complete search history.

(56) References Cited

U.S. PATENT DOCUMENTS

2013/0041218 A1*  2/2013  Iida ................... A61B 1/00006
                                                  600/109
2014/0203170 A1*  7/2014  Ono ....................... A61B 1/045
                                                  250/208.1

FOREIGN PATENT DOCUMENTS

JP    2004-212873 A    7/2004
JP    2007-111151 A    5/2007
(Continued)

OTHER PUBLICATIONS

Machine translation of JP 2004-212873 (Year: 2004).*
(Continued)

*Primary Examiner* — Alexandra L Newton
(74) *Attorney, Agent, or Firm* — Scully, Scott, Murphy & Presser, P.C.

(57) ABSTRACT

An imaging system includes an illumination portion, an imager, a reader, and an illumination controller configured to control an intensity of illumination light based on modulated illumination in a non-reading period. The modulated illumination has a first integrated light amount as a product of a variable intensity of a first pulse and an output period of the illumination light and a second integrated light amount as a product of a constant intensity of a second pulse and the output period. In the non-reading period, the illumination controller causes a predetermined light amount that is not larger than a maximum value of the first integrated light amount and is not smaller than a minimum value of the second integrated light amount to transit between the first integrated light amount and the second integrated light amount.

20 Claims, 15 Drawing Sheets

(51) Int. Cl.
   *A61B 1/07*    (2006.01)
   *G02B 23/24*   (2006.01)
   *H04N 5/225*   (2006.01)
   *A61B 1/05*    (2006.01)
   *A61B 1/04*    (2006.01)
   *A61B 1/045*   (2006.01)

(52) U.S. Cl.
   CPC ........ *A61B 1/00188* (2013.01); *G02B 23/243* (2013.01); *H04N 2005/2255* (2013.01)

(56) References Cited

FOREIGN PATENT DOCUMENTS

JP   2011-072424 A    4/2011
WO   WO 2013/175908 A1   11/2013

OTHER PUBLICATIONS

International Search Report dated Oct. 13, 2015 issued in PCT/JP2015/070920.
Japanese Office Action dated Jan. 22, 2019 in Japanese Patent Application No. 2017-529245.
English translation of International Preliminary Report on Patentability dated Feb. 1, 2018 together with the Written Opinion received in related International Application No. PCT/JP2015/070920.

* cited by examiner

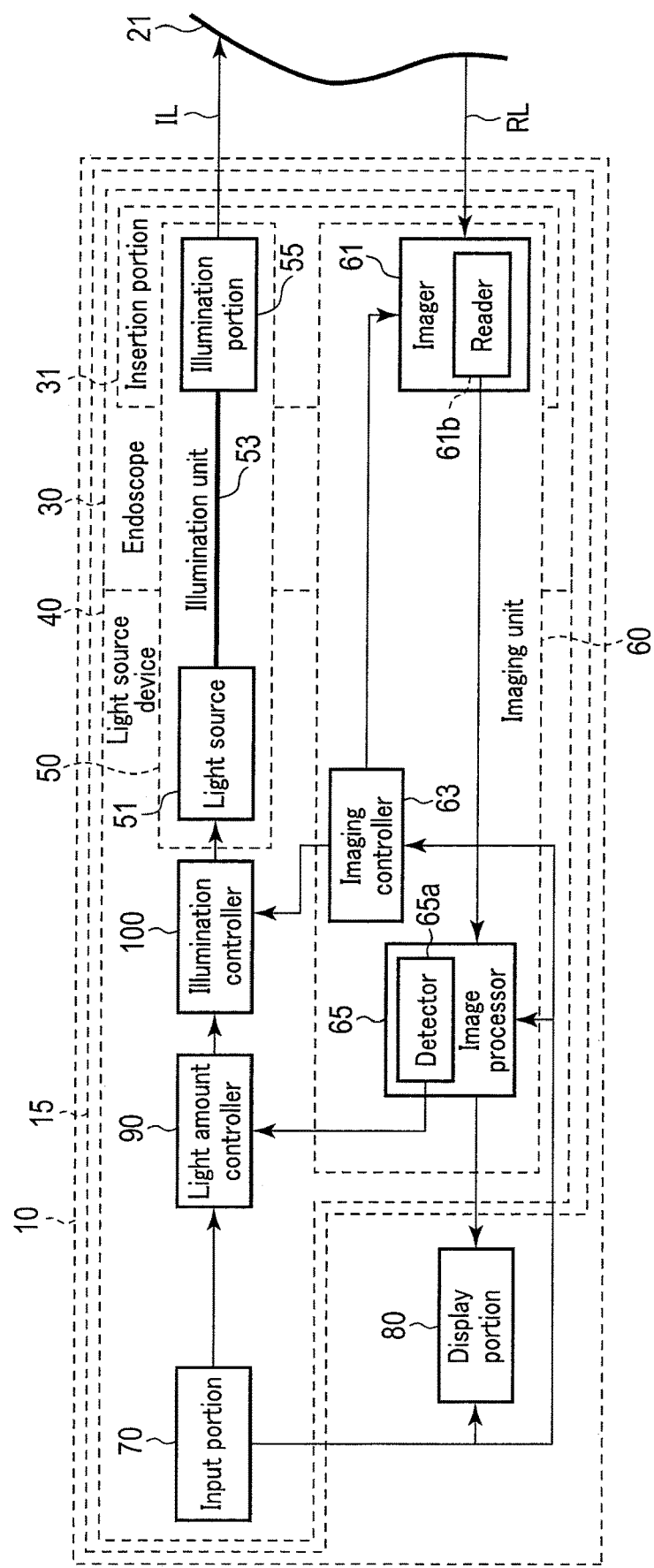
F I G. 2B

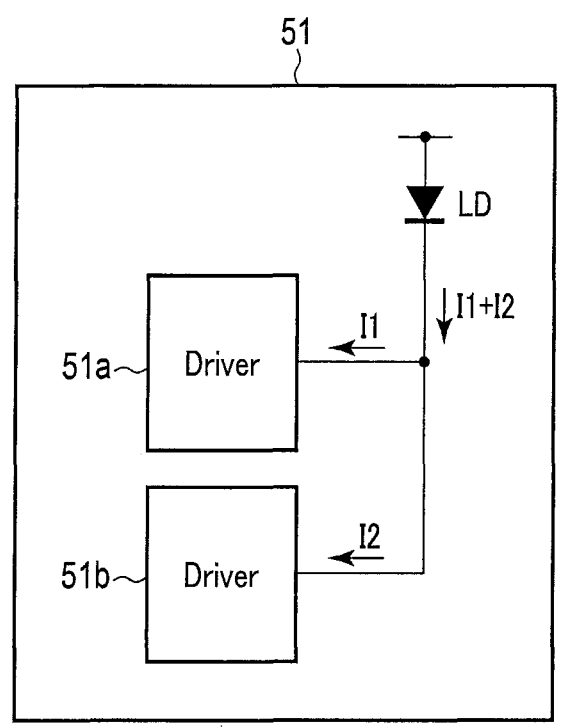
F I G. 2C

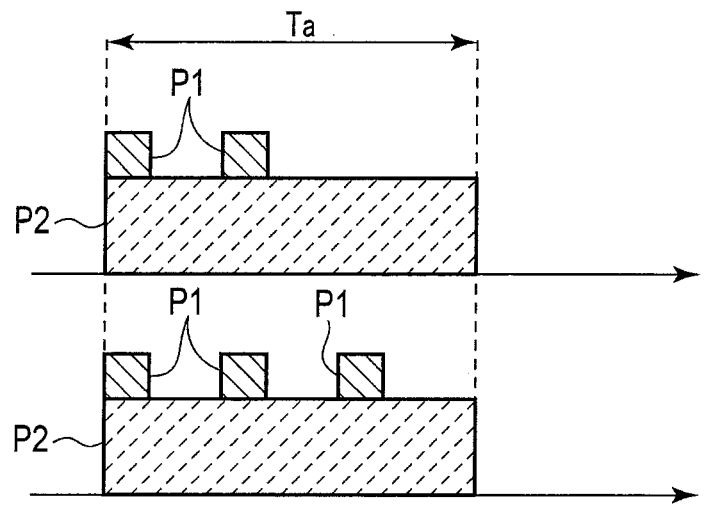
F I G. 5C
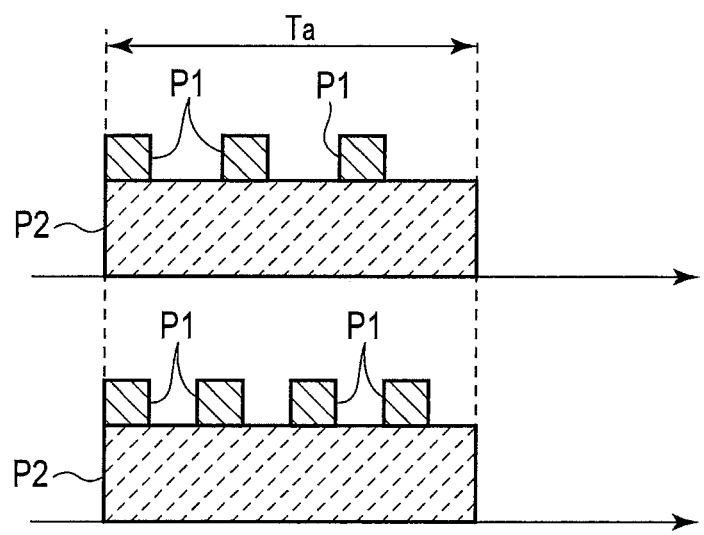
F I G. 5D

IMAGING SYSTEM AND ENDOSCOPE SYSTEM

CROSS-REFERENCE TO RELATED APPLICATIONS

This application is a Continuation Application of PCT Application No. PCT/JP2015/070920, filed Jul. 23, 2015, the entire contents of all of which are incorporated herein by references.

BACKGROUND OF THE INVENTION

1. Field of the Invention

The present invention relates to an imaging system and an endoscope system.

2. Description of the Related Art

For example, Jpn. Pat. Appln. KOKAI Publication No. 2007-111151 discloses an endoscope including a light source that is turned on by a pulse.

A recent imaging device uses, for example, a CMOS type image sensor (to be referred to as a CMOS hereinafter). The CMOS generally adopts a rolling shutter scheme for sequentially reading pixel signals for each horizontal line. In this case, a state in which there exist lines being exposed and lines not being exposed at the same time occurs.

BRIEF SUMMARY OF THE INVENTION

One embodiment of the present invention is an imaging system comprising an illumination portion configured to emit illumination light with which a main target is illuminated; an imager including pixels two dimensionally arrayed and each configured to generate an electrical signal by photoelectrically converting received light; a reader having a reading period during which some part of lines of the pixels are read in one of one frame period and one field period and configured to sequentially read the electrical signals generated by the pixels for each line of the pixels; and an illumination controller configured to control an intensity of the illumination light based on modulated illumination for modulating the intensity of the illumination light in a non reading period as a period other than the reading period, wherein in the non reading period, the modulated illumination has a first integrated light amount as a product of a variable intensity of a first pulse and an output period of the illumination light and a second integrated light amount as a product of a constant intensity of a second pulse and the output period, and in the non reading period, the illumination controller causes a predetermined light amount that is not larger than a maximum value of the first integrated light amount and is not smaller than a minimum value of the second integrated light amount to transit between the first integrated light amount and the second integrated light amount.

One embodiment of the present invention is an endoscope system comprising an imaging system as describe above and including an endoscope and a light source device from which the endoscope is detachable.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 2B is a schematic block diagram showing an endoscope system according to the first embodiment of the present invention;

FIG. 2C is a block diagram showing the configuration of drivers of a light source;

FIG. 5C is a timing chart showing an example of an increase/decrease in output period of the pulse P1, and showing PNM control;

FIG. 5D is a timing chart showing an example of an increase/decrease in output period of the pulse P1, and showing PDM control;

DETAILED DESCRIPTION OF THE INVENTION

Embodiments of the present invention will be described in detail below with reference to the accompanying drawings. Note that for the sake of illustrative clarity, some drawings omit illustrations of some members.

First Embodiment

Figure 1:
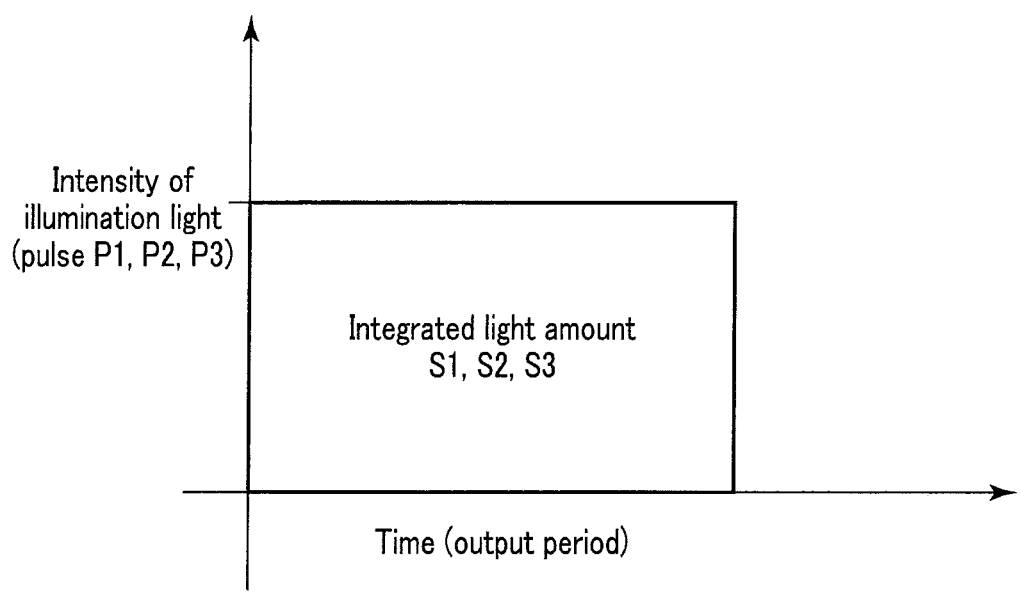
FIG. 1 is a graph showing an integrated light amount (the light amount of illumination light) as a product of the intensity of the illumination light and an output period.

The first embodiment will be described with reference to FIGS. 1, 2A, 2B, 2C, 3, 4A, 4B, 4C, 4D, 4E, and 4F. Note that as shown in FIG. 1, each integrated light amount S1, S2, or S3 is defined as the product of the intensity (to be referred to as the light intensity hereinafter) of illumination light IL as a pulse P1, P2, or P3 and an output period serving as an illumination time. That is, each integrated light amount S1, S2, or S3 indicates the light amount of the illumination light.

Figure 2A:
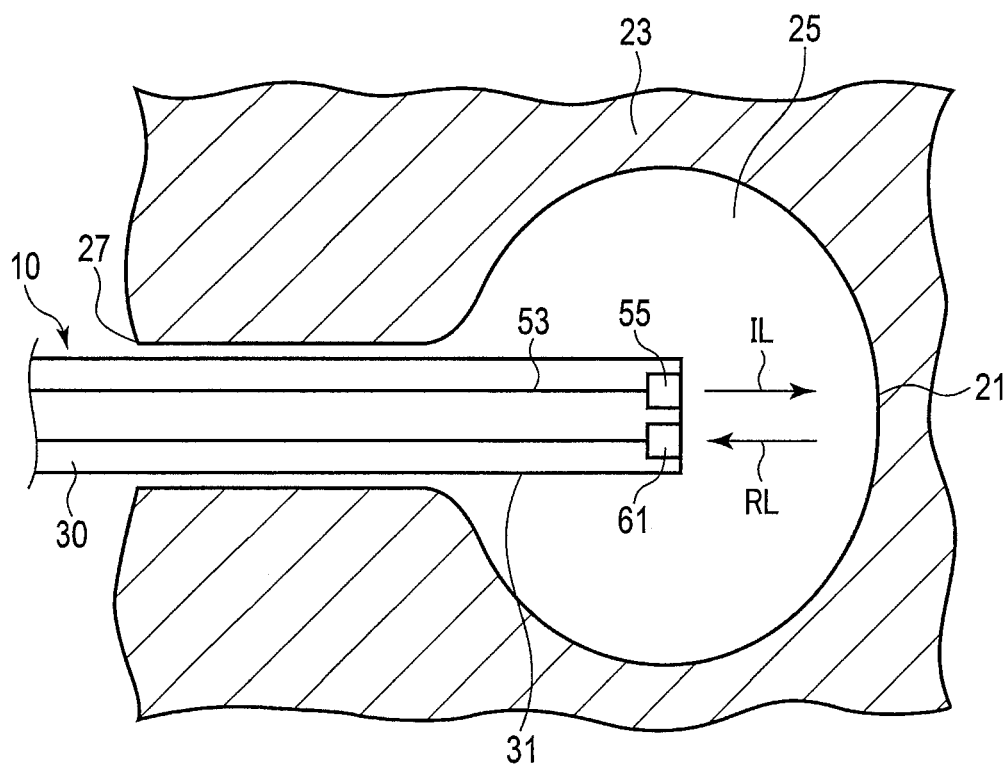
FIG. 2A is a view showing an insertion portion inserted into an internal space where external light is difficult to enter.

As shown in FIG. 2A, an endoscope system 10 is an example of an observation system for observing a main target 21 existing in a dark portion where external light is difficult to reach and enter. The dark portion is, for example, an internal space (internal space portion) 25 of an observation target 23. The observation target 23 has a narrow entrance (narrow entrance portion) 27 connected to the internal space 25. The internal space 25 exists in the back of the narrow entrance 27, and is wider than the entrance 27. External light such as indoor light or sunlight is difficult to reach and enter the internal space 25. That is, since external light is difficult to enter the internal space 25, the internal space 25 is a portion that is difficult to be illuminated with external light.

As shown in FIGS. 2A and 2B, the endoscope system 10 includes an imaging system 15. The imaging system 15 includes an endoscope 30, and a light source device 40 from which the endoscope 30 is detachable. The endoscope 30 includes an insertion portion 31 that is inserted into the internal space 25 as a dark portion. The insertion portion 31 includes an illumination portion 55 and an imager (image portion) 61 (both of which will be described later) both of which are provided in a distal end portion of the insertion portion 31. The imaging system 15 illuminates the main target 21 with the illumination light IL from the illumination portion 55, and causes the imager 61 to image light RL reflected by the main target 21. The insertion portion 31 has a shape that is readily inserted into the internal space 25 of the observation target 23. For example, the insertion portion 31 is cylindrical shape. When the insertion portion 31 is inserted into the internal space 25, the entrance 27 is mostly closed by the insertion portion 31, and thus external light is more difficult to enter the internal space 25. That is, most of illumination light with which the internal space 25 including the main target 21 is illuminated is the illumination light IL emitted from the illumination portion 55. Therefore, in this embodiment, in a status in which the endoscope system 10 is used, it is almost unnecessary to consider external light, as compared to the illumination light IL emitted from the illumination portion 55.

For example, the insertion portion 31 has a tubular shape, and is long, narrow, and flexible. The insertion portion 31 can actively bend by an operation of an operation portion (not shown) connected to the insertion portion 31. In addition, when the insertion portion 31 receives an external force, it can passively bend by the external force.

Note that the endoscope 30 is separated from the light source device 40 and is detachable from the light source device 40. However, the present invention need not be limited to this. The endoscope 30 may incorporate the light source device 40.

As shown in FIG. 2B, the imaging system 15 includes an illumination unit 50 for illuminating the main target 21 with the illumination light IL, and an imaging unit 60 for imaging the light RL reflected by the main target 21 that has been illuminated with the illumination light IL.

The imaging system 15 includes an input portion 70 for inputting an operation start instruction to each of the illumination unit 50, the imaging unit 60, and a display portion 80 (to be described later). The endoscope system 10 includes the display portion 80 for displaying, as an image, the reflected light RL imaged by the imaging unit 60. The input portion 70 may input the target value of the luminance value of the illumination light IL or the target value of the light amount of the illumination light. The input portion 70 is provided in, for example, the light source device 40, and the display portion 80 is separated from the endoscope 30 and the light source device 40. The input portion 70 includes, for example, a switch or touch panel. The display portion 80 includes, for example, a monitor.

The imaging system 15 includes a light amount controller (light amount control portion) 90 for outputting, based on a luminance signal output from a detector (detecting portion) 65a (to be described later) of the imaging unit 60, a light amount control signal that controls the light amount of the illumination light, and an illumination controller (illumination control portion) 100 for controlling the driving timing of a light source (light source portion) 51 and the intensity of the illumination light IL based on the light amount control signal output from the light amount controller 90 and an all-line exposure signal output from an imaging controller (imaging control portion) 63 (to be described later) of the imaging unit 60. The light amount controller 90 and the illumination controller 100 are provided in the light source device 40.

As shown in FIG. 2B, the illumination unit 50 includes the light source 51 for emitting primary light, a light guide (light guide member) 53 for guiding the primary light emitted from the light source 51, and the above-described illumination portion 55. The light source 51 is provided in the light source device 40, the light guide 53 is provided in the light source device 40 and the endoscope 30, and the illumination portion 55 is provided in the distal end portion of the insertion portion 31.

The light source 51 includes, for example, a laser diode for emitting a laser beam as primary light. As shown in FIG. 2C, the light source 51 is driven by drivers 51a and 51b each including a circuit. The drivers 51a and 51b are of, for example, a current addition type. In this case, for example, the drivers 51a and 51b generate current values I1 and I2 corresponding to the pulses P1 and P2 (to be described later), respectively. The drivers 51a and 51b generate the current values I1 and I2 corresponding to the pulses P1 and P2, respectively, so that a current value corresponding to the pulse P3 as the sum of the current values respectively corresponding to the pulses P1 and P2. The drivers 51a and 51b may be of a current output type. The light guide 53 includes, for example, an optical fiber.

The illumination portion 55 includes an optical converter (optical convert member) for converting the primary light guided by the light guide 53 into secondary light having optical characteristics different from the optical characteristics of the primary light. The optical converter emits the secondary light as the illumination light IL with which the main target 21 is illuminated. The illumination portion 55 may include, for example, a phosphor for emitting fluorescence (secondary light) using the primary light as excitation light. That is, the illumination portion 55 converts the wavelength (the optical characteristics) of the primary light. The illumination portion 55 may have a function of, if the primary light is a laser beam, adjusting the distribution of the primary light to increase the spread angle of the primary light. The illumination portion 55 may scatter or diffuse the primary light. The illumination portion 55 may have a function of, if the primary light is a laser beam, converting the phase of the primary light to reduce coherence, and thus preventing a speckle from occurring.

As shown in FIG. 2B, the imaging unit 60 includes the above-described imager 61, the imaging controller 63 for controlling the imager 61, and an image processor (image processing portion) 65 for generating a color image of the main target 21 by image processing for electrical signals output from the pixels of the imager 61. The imager 61 is provided in the distal end portion of the insertion portion 31 to be adjacent to the illumination portion 55. The imaging controller 63 and the image processor 65 are provided in the light source device 40.

The imager 61 is of a CMOS type, and receives the reflected light RL, and outputs, as electrical signals, image information corresponding to the reflected light RL to the image processor 65. More specifically, the imager 61 includes the pixels two-dimensionally arrayed. Each pixel generates an electrical signal having image information by photoelectrically converting the received reflected light RL.

The imager 61 includes a reader (reading portion) 61b for sequentially reading the electrical signals generated by the pixels for each horizontal line of the pixels. The reader 61b has a reading period during which the reader 61b reads at least part of the horizontal lines of the pixels in one (single) frame period Tf1 (see FIG. 3). Note that Tf1 indicates the one frame period but may indicate one (single) field period. The imager 61 need not be limited to the CMOS type, and may have another arrangement using the same reading method.

The imaging controller 63 controls the imager 61 to sequentially start exposure of the imager 61 in the one frame period Tf1 for each horizontal line. The one frame period Tf1 and the one field period each indicate, for example, a period during which one image is captured. The imaging controller 63 controls the imager 61 so that the reader 61b of the imager 61 reads, for each horizontal line, horizontal lines for which a predetermined exposure period (Tr+Ta (see FIG. 3)) has elapsed since the start of exposure. That is, the imaging controller 63 executes exposure control by the rolling shutter. The imaging controller 63 sets the exposure period (Tr+Ta) to be longer than a reading period (to be referred to as a reading period Tr hereinafter (see FIG. 3)) necessary to read all the horizontal lines. This causes the reader 61b of the imager 61 to read the first horizontal line after the imager 61 starts exposure for the last horizontal line. The imaging controller 63 controls exposure of the imager 61 so that the reading period Tr and an all-line exposure period Ta (see FIG. 3) during which all the horizontal lines are simultaneously exposed.

The image processing by the image processor 65 includes demosaicing (synchronization) for a single-CCD color image of a plurality of colors included in the electrical signals (image information) output from the imager 61, generation of a color image by demosaicing, and color balance adjustment, gamma conversion, and color conversion for the color image. The color image indicates a three-CCD color image in which R, G, and B color signals are included for each pixel. The image processor 65 outputs the color image having undergone the image processing to the display portion 80. The display portion 80 displays the color image. Note that the display portion 80 may display a monochrome image.

The image processor 65 includes the detector 65a for detecting the luminance value of the main target 21 included in the color image. The detector 65a outputs a luminance signal having the luminance value to the light amount controller 90.

The imaging controller 63, the image processor 65, the light amount controller 90, and the illumination controller 100 are formed by, for example, a hardware circuit including an ASIC. At least one of the imaging controller 63, the image processor 65, the light amount controller 90, and the illumination controller 100 may be formed by, for example, a processor including a CPU. If at least one of these portions is formed by a processor, an internal memory or external memory (neither of which is shown) accessible by the processor is arranged. The internal memory or external memory stores a program code that, when executed by the processor, causes the processor to function as at least one of the above portions. Furthermore, the imaging controller 63, the image processor 65, the light amount controller 90, and the illumination controller 100 may be formed using one processor or a plurality of processors. In the latter case, the plurality of processors can transmit/receive data to perform processing in cooperation with each other. In addition, in the latter case, the plurality of processors can be arranged in different housings.

The relationship among the exposure timing of the imager 61, the all-line exposure signal, and the intensity waveform of the illumination light will be described with reference to FIG. 3.

The imager 61 starts exposure by resetting the respective pixels for each horizontal line. The reset timing is represented by RST in FIG. 3. The reader 61b of the imager 61 sequentially reads the electrical signals as image information from horizontal lines for which the exposure period (Tr+Ta) has elapsed since the start of exposure. The imager 61 ends exposure by reading. The reading timing is represented by RD in FIG. 3. In the exposure period (Tr+Ta), as described above, Tr represents the reading period necessary to read all the horizontal lines, and Ta represents the all-line exposure period during which all the horizontal lines are simultaneously exposed. In the all-line exposure period Ta, not reading but exposure is performed. The all-line exposure period Ta is a non-reading period.

Figure 3:
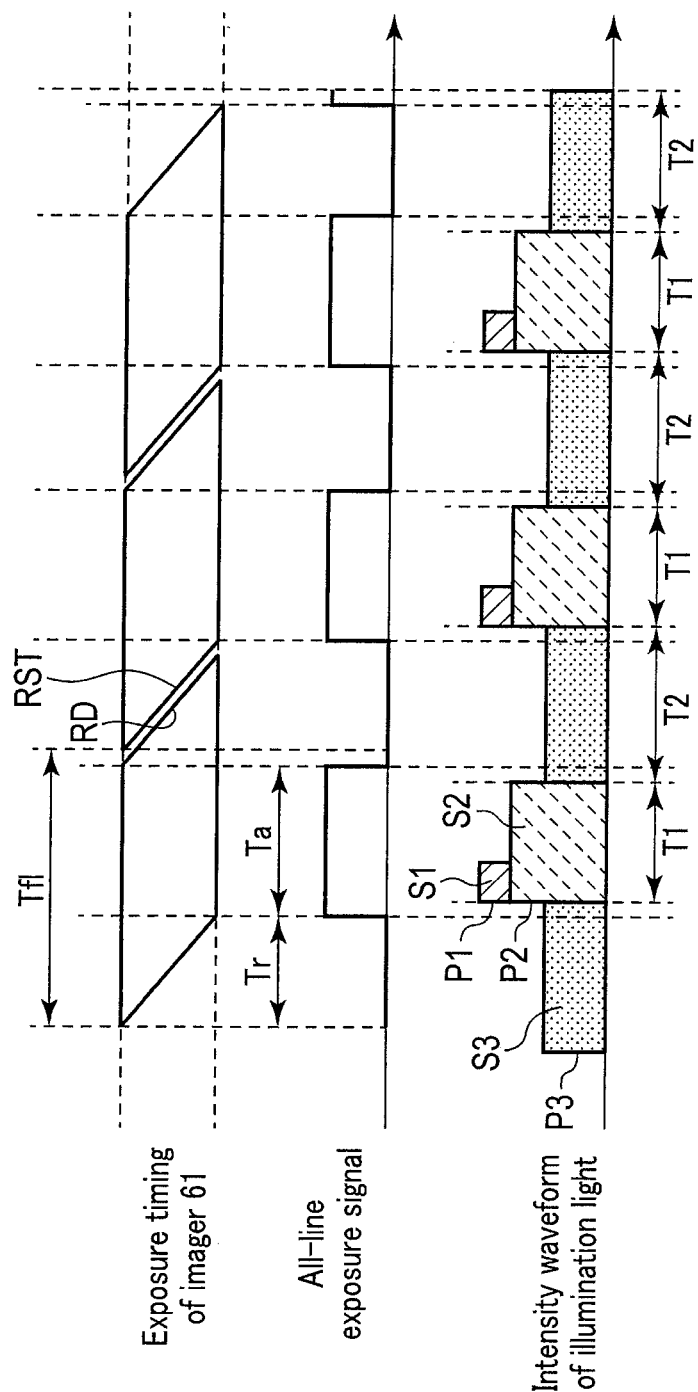
FIG. 3 is a timing chart showing the relationship among an exposure timing of an imager, an all-line exposure signal, and the intensity waveform of illumination light.

As shown in FIG. 3, the exposure period (Tr+Ta) is shorter than the one frame period Tf1 of the imager 61. Note that the exposure period (Tr+Ta) may be equal to the one frame period Tf1.

As described above, since the exposure period (Tr+Ta) is longer than the reading period Tr, the all-line exposure period Ta is positive (Ta>0). Thus, the imager 61 starts exposure of the last horizontal line before the reader 61b starts reading of the horizontal line whose exposure has been started first. A period in which at least one horizontal line is exposed but which is not the all-line exposure period Ta, for example, the reading period Tr is a non-all-line exposure period.

As shown in FIG. 3, the imaging controller 63 generates, as an all-line exposure signal, for example, a signal that is set at high level in the all-line exposure period Ta, and generates, as an all-line exposure signal, for example, a signal that is set at low level in a period other than the all-line exposure period Ta. The imaging controller 63 outputs the all-line exposure signal to the illumination controller 100. The light amount controller 90 generates a light amount control signal based on the luminance signal output from the detector 65a, and outputs the light amount control signal to the illumination controller 100. Note that the light amount controller 90 generates a light amount control signal so that the luminance value contained in the luminance signal is approximated to, for example, the target value of the luminance value input from the input portion 70. The light amount control signal has information indicating that the light amount of the illumination light maintains the current state or how much the light amount of the illumination light increases/decreases with respect to the current state.

The light amount control signal may be a signal indicating a difference value. The difference value is a value obtained by subtracting the target value of the luminance value from the luminance value detected by the detector 65a. Alternatively, the light amount control signal may be a signal indicating a light amount ratio. The light amount ratio is, for example, a value obtained by dividing the detected luminance value by the target value of the luminance value.

Note that the light amount control signal need not be limited to the signal based on the luminance value. Any method of generating a light amount control signal can be used as long as the light amount controller 90 can control the light amount of the primary light so that the light amount of the first primary emitted from the light source 51 is approximated to the target value of the light amount input from the input portion 70.

The light amount controller 90 may output the light amount control signal to the illumination controller 100 when, for example, a predetermined time elapses since the start of the all-line exposure period Ta.

The illumination controller 100 sets the illumination light intensities (to be referred to as intensities hereinafter) of the pulses P1, P2, and P3 based on the light amount control signal output from the light amount controller 90 and the all-line exposure signal output from the imaging controller 63. The illumination controller 100 sets, in accordance with the intensities of the pulses P1, P2, and P3, a current value to be applied to the light source 51. Then, the illumination controller 100 applies the current value to the light source 51. The magnitude of the current value influences the intensity of the illumination light IL. In this way, the illumination controller 100 controls an increase/decrease in light amount of the illumination light IL based on, for example, the light amount control signal generated based on the luminance value detected by the detector 65a.

Referring to FIG. 3, the illumination controller 100 performs continuous illumination in at least part of the reading period Tr in the one frame period Tf1 or one field period, and performs modulated illumination in the all-line exposure period Ta as a period other than the reading period. Modulated illumination is performed in a first period T1 of the all-line exposure period Ta. Therefore, continuous illumination is performed in a second period T2 other than the first period T1. To provide a margin to deviation of timing control or the like, the first period T1 is slightly shorter on the start timing side and end timing side of the all-line exposure period Ta with respect to the entire all-line exposure period Ta. Note that if it is not necessary to provide a margin, the first period T1 coincides with the all-line exposure period Ta.

Continuous illumination keeps the intensity of the illumination light IL constant. Modulated illumination modulates the intensity of the illumination light IL. The intensity of the illumination light IL in modulated illumination has a waveform obtained by combining, with the pulse P2 for keeping the intensity of the illumination light IL constant in the all-line exposure period Ta as a non-reading period, the pulse P1 for the integrated light amount S1 that changes along with an increase/decrease in output period as a period during which the illumination light IL is output in the all-line exposure period Ta as a non-reading period. The output period corresponds to 0% to 100% of the first period T1. In modulated illumination, the light amount of the illumination light is controlled by the sum of the integrated light amount S1 in the pulse P1 and the integrated light amount S2 in the pulse P2. The intensity of the illumination light IL in continuous illumination corresponds to the pulse P3. In continuous illumination, the light amount of the illumination light is controlled by the integrated light amount S3 in the pulse P3. The illumination controller 100 controls the intensity of the illumination light IL in the one frame period Tf1 or one field period based on continuous illumination and modulated illumination. The illumination controller 100 controls an increase/decrease in light amount of the illumination light output in the one frame period Tf1 or one field period by controlling the intensity of the illumination light IL based on continuous illumination and modulated illumination.

The integrated light amount S1 in the pulse P1 is given by the value of the product of the intensity of the pulse P1 and the output period. The integrated light amount S2 in the pulse P2 is given by the value of the product of the intensity of the pulse P2 and the first period T1. The integrated light amount S3 in the pulse P3 is given by the value of the product of the intensity of the pulse P3 and the second period T2.

The light source 51 emits a laser beam as the primary light. The light guide 53 guides the primary light to the illumination portion 55. The illumination portion 55 converts the optical characteristics of the primary light, and the main target 21 is illuminated with primary light as the illumination light IL.

The imager 61 images the light RL reflected by the main target 21. At this time, the pixels respectively output electrical signals by photoelectrically converting the reflected light RL. The reader 61b sequentially reads the electrical signals for each horizontal line of the pixels. The imaging controller 63 outputs an all-line exposure signal to the illumination controller 100. The display portion 80 displays an image based on the electrical signals.

The detector 65a detects the luminance value of a main target 21a based on the electrical signals output from the pixels, and outputs a luminance signal to the light amount controller 90. The light amount controller 90 generates a light amount control signal based on the luminance signal, and outputs the light amount control signal to the illumination controller 100.

The illumination controller 100 sets, based on the light amount control signal output from the light amount controller 90 and the all-line exposure signal output from the imaging controller 63, the shapes of the pulses P1, P2, and P3, for example, their intensities and output periods. In accordance with the intensities of the pulses P1, P2, and P3, the illumination controller 100 sets a current value to be applied to the light source 51. The illumination controller 100 applies the current value to the light source 51. The light amount of the illumination light is controlled via the total light amount of the primary light emitted from the light source 51 controlled by the current value. For example, the illumination controller 100 increases or decreases the light amount of the illumination light in accordance with the increase/decrease value of the light amount indicated by the light amount control signal.

Control of the light amount of the illumination light will be described below with reference to FIGS. 3, 4A, 4B, 4C, 4D, 4E, and 4F.

A case in which if the light amount of the illumination light is controlled, the light amount control signal has information indicating that the light amount of the illumination light increases with respect to the current state will be described below with reference to FIGS. 4A, 4B, 4C, and 4D.

Assume that only the pulse P1 is set while the integrated light amounts S1, S2, and S3 in the pulses P1, P2, and P3 are 0. The illumination controller 100 controls the intensity of the pulse P1 as an intensity of a constant value to 1/M (M is an integer of 2 or more) of a maximum intensity Pmax of the illumination light. In this embodiment, $M=2^2=4$ is set. Note that the illumination controller 100 may form the pulse P1 by a plurality of pulses in the one frame period Tf1 or one field period. As described above, since the intensity of the pulse P1 has a constant value, the integrated light amount S1 in the pulse P1 is controlled by adjusting the output period of the pulse P1. Adjustment and control are performed by the illumination controller 100. The output period corresponds to 0% to 100% of the first period T1. Since the light amount of the illumination light increases with respect to the current state, the output period increases. Note that the output period is set to 0% to 100% of the first period T1. However, the minimum value of the output period may be a value (for example, 5% of the first period T1) other than 0%, and the maximum value of the output period may be a value (for example, 95% of the first period T1) other than 100%.

Figure 4A:
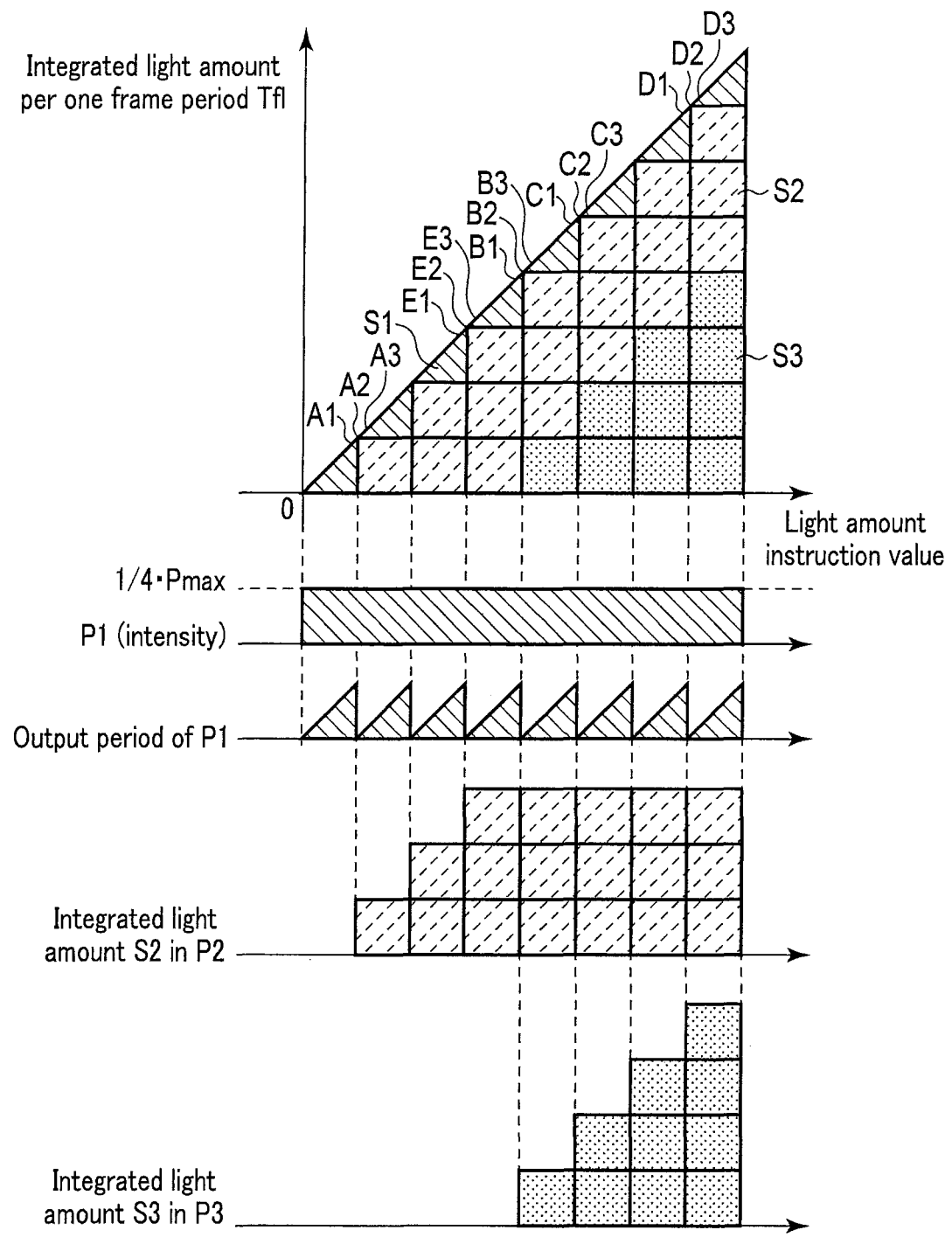
FIG. 4A shows graphs showing the relationship among an integrated light amount per one frame period, a pulse P1, an integrated light amount in the pulse P1, an integrated light amount in a pulse P2, and an integrated light amount in a pulse P3 according to the first embodiment.
Figure 4B:
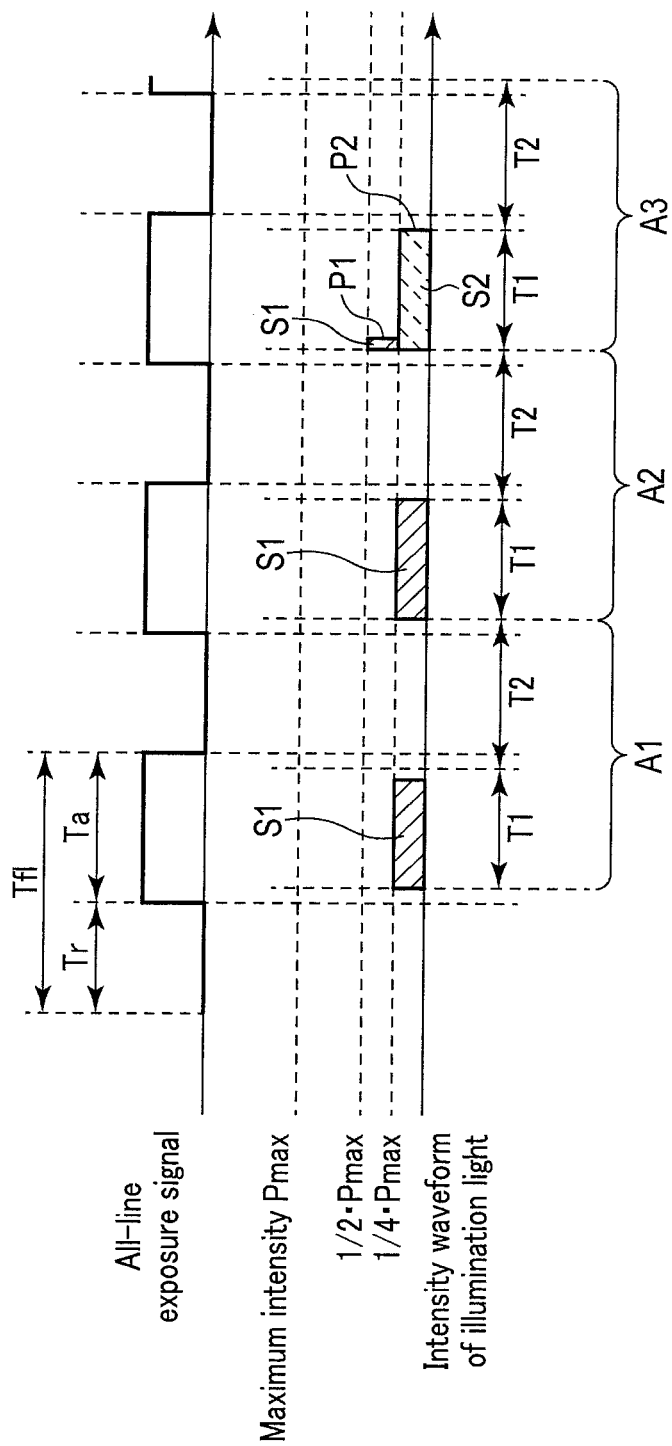
FIG. 4B is a timing chart, showing the relationship among the all-line exposure signal, the intensity waveform of the illumination light, and the integrated light amount at each of points A1, A2, and A3 shown in FIG. 4A, for explaining an example in which the integrated light amount in the pulse P1 transits to the integrated light amount in the pulse P2 along with an increase in light amount of the illumination light.

In a period from a point A1 to a point A2 in FIGS. 4A and 4B, the pulse P1 is output in 0% to 100% of the first period T1. For example, at the point A1, the output period of the pulse P1 falls within the range of 0% (inclusive) to 100% (inclusive) of the first period T1. For example, at the point A2, the output period of the pulse P1 corresponds to 100% of the first period T1. The illumination controller 100 controls an increase/decrease in output period. The integrated light amount S1 is the product of the intensity of the pulse P1 and the output period, as described above, and is calculated by the illumination controller 100. In the period from the point A1 to the point A2, therefore, the minimum integrated light amount is the product of the intensity of the pulse P1 and the minimum value of the output period (in this embodiment, 0% of T1), and the maximum integrated light amount is the product of the intensity of the pulse P1 and the maximum value of the output period (in this embodiment, 100% of T1). For example, at the point A2, the integrated light amount S1 is given by Pmax/4×T1, and is the maximum integrated light amount. As described above, the illumination controller 100 increases/decreases the integrated light amount S1 in the pulse P1 between the maximum integrated light amount and the minimum integrated light amount by increasing/decreasing the output period, thereby increasing/decreasing the integrated light amount (the light amount of the illumination light).

Next, a case in which after the output period of the pulse P1 reaches 100% of the first period T1 (the integrated light amount S1 in the pulse P1 reaches the maximum integrated light amount) at the point A2 shown in FIGS. 4A and 4B, the light amount of the illumination light further increases at a point A3 or the like will be explained.

In this case, as shown in FIG. 4B, the integrated light amount S1 in the pulse P1 at the point A2 transits to the integrated light amount S2 in the pulse P2 in the first period T1 after the point A2 including the point A3. Transition indicates that the integrated light amount S1 in the pulse P1 as a transition source is decreased by a predetermined amount, and the integrated light amount S2 in the pulse P2 as a transition destination is added (increased) with the predetermined amount. The predetermined amount is, for example, a transition amount, the difference between the above-described maximum and minimum integrated light amounts, and the maximum integrated light amount in the pulse P1 at the point A2. The predetermined amount will be referred to as a unit transition integrated light amount hereinafter. The predetermined amount decreasing and addition operations are performed at the same time. This means that the decreasing and addition operations are performed during one frame period Tf1. The illumination controller 100 performs such transition.

In this case, the integrated light amount S1 in the pulse P1 at the point A2 is given by Pmax/4×T1, the integrated light amount S2 in the pulse P2 at the point A2 is 0, and the difference between the maximum and minimum integrated light amounts as the predetermined amount is given by Pmax/4×T1.

Although not shown, in a period after the point A2 including the point A3, since Pmax/4×T1 is decreased by Pmax/4×T1 as the predetermined amount (transition amount), the integrated light amount S1 in the pulse P1 as a transition source becomes 0. In the period after the point A2 including the point A3 shown in FIGS. 4A and 4B, since Pmax/4×T1 as the predetermined amount (transition amount) is added to 0, the integrated light amount S2 in the pulse P2 as a transition destination becomes Pmax/4×T1. The illumination controller 100 sets the intensity of the pulse P2 to Pmax/4 so that the integrated light amount S2 in the pulse P2 becomes Pmax/4×T1. The illumination controller 100 sets the intensity of the pulse P1 to Pmax/4 so that the integrated light amount S1 in the pulse P2 can be adjusted within the range of 0 to Pmax/4×T1 by the output period.

Next, in the period after the point A2 including the point A3, the intensity of the pulse P1 becomes Pmax/4. After that, if the light amount of the illumination light further increases in the period after the point A2 including the point A3, as shown in FIGS. 4A and 4B, the output period of the pulse P1 increases from 0% of the first period T1 to 100%.

In a period after the point A3 as well, every time the output period of the pulse P1 reaches 100% of the first period T1 again, the operations at the points A2 and A3 are repeated.

As described above, if the illumination controller 100 further increases the light amount of the illumination light in the one frame period Tf1 or one field period while the integrated light amount S1 in the pulse P1 is the maximum integrated light amount at the points A2 and A3, the illumination controller 100 performs the first increasing transition operation of decreasing the integrated light amount S1 in the pulse P1 by the transition amount, and increasing the integrated light amount S2 in the pulse P2 by the transition amount. The illumination controller 100 sets the intensity of the pulse P1 and that of the pulse P2 based on the integrated light amounts S1 and S2 after transition. The illumination controller 100 sets the transition amount as the difference between the maximum and minimum integrated light amounts. At the point A3 after the first increasing transition operation, the illumination controller 100 adjusts the output period of the pulse P1 so that the increase amount of the light amount of the illumination light corresponds to the integrated light amount S1 in the pulse P1.

Figure 4C:
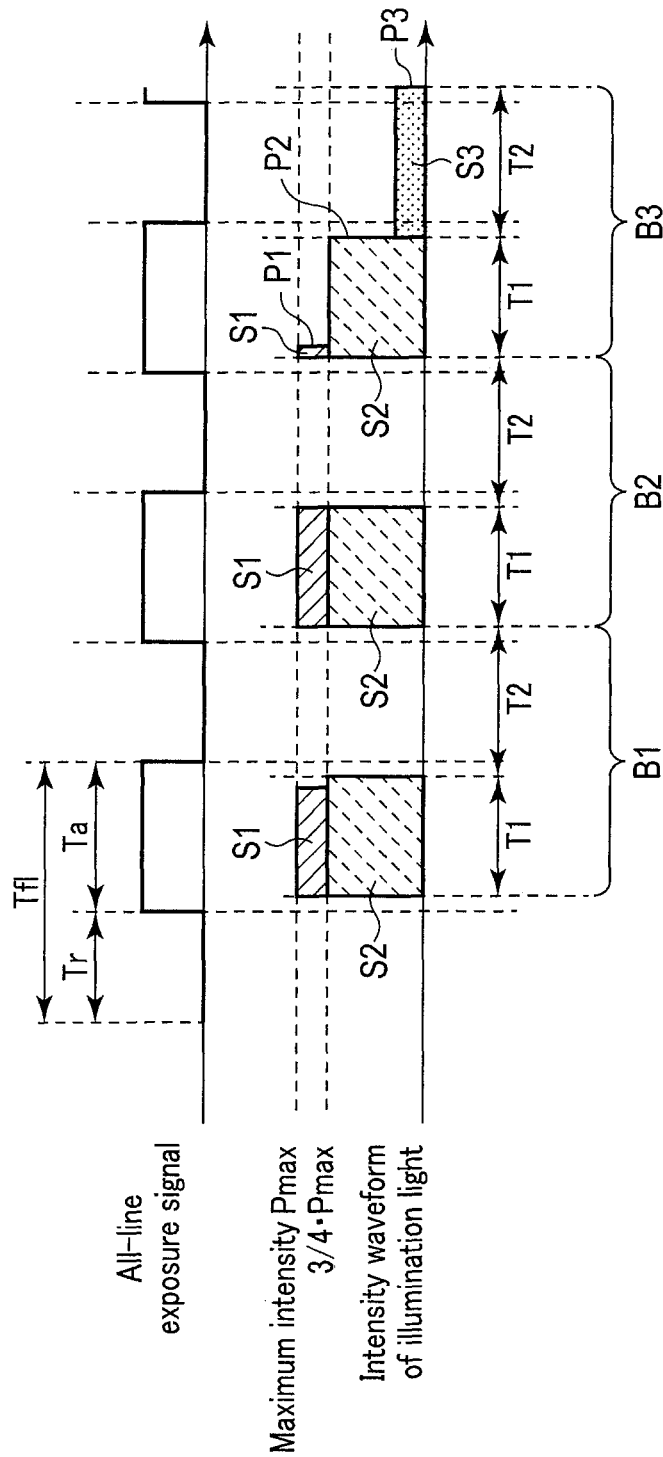
FIG. 4C is a timing chart, showing the relationship among the all-line exposure signal, the intensity waveform of the illumination light, and the integrated light amount at each of points B1, B2, and B3 shown in FIG. 4A, for explaining an example in which along with an increase in light amount of the illumination light, the integrated light amount in the pulse P1 transits to the integrated light amount in the pulse P2 and the integrated light amount in the pulse P2 transits to the integrated light amount in the pulse P3.
Figure 4D:
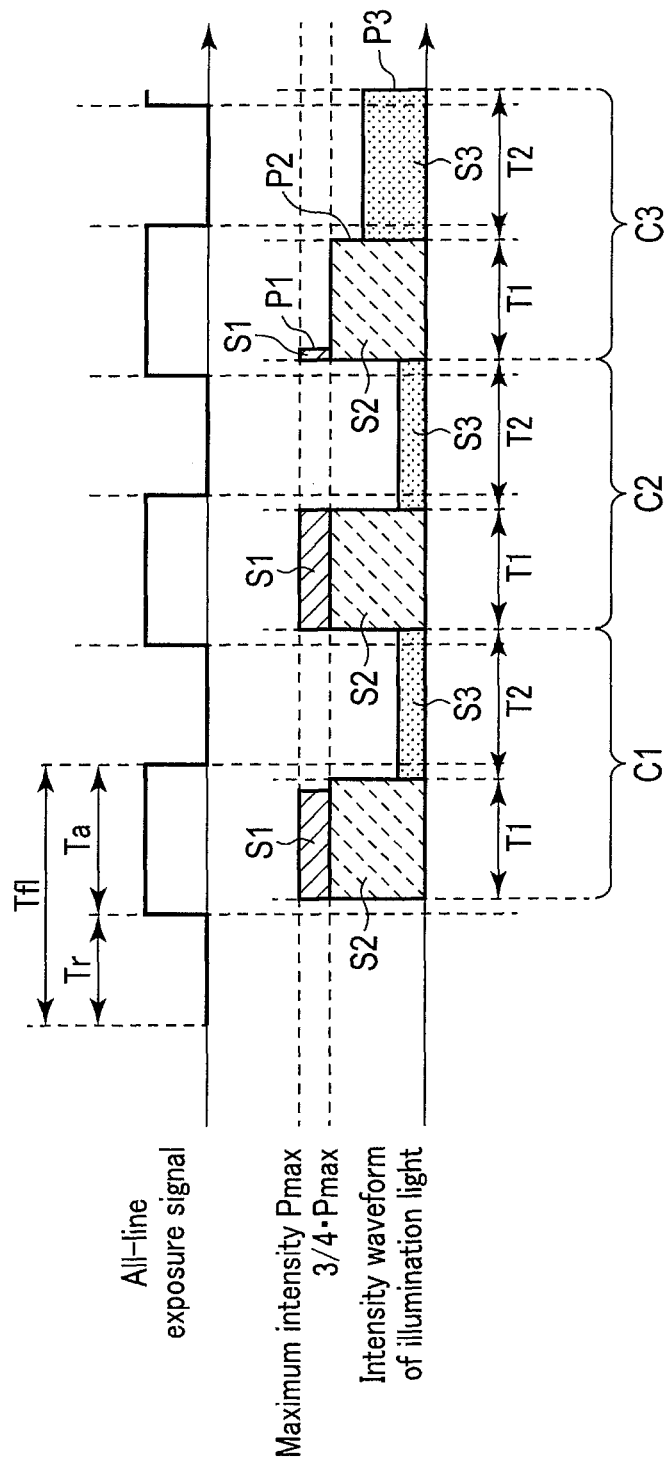
FIG. 4D is a timing chart, showing the relationship among the all-line exposure signal, the intensity waveform of the illumination light, and the integrated light amount at each of points C1, C2, and C3 shown in FIG. 4A, for explaining an example in which along with an increase in light amount of the illumination light, the integrated light amount in the pulse P1 transits to the integrated light amount in the pulse P2 and the integrated light amount in the pulse P2 transits to the integrated light amount in the pulse P3.

Next, if the operation is repeated, the sum of the intensity (Pmax/4) of the pulse P1 and that (Pmax×3/4) of the pulse P2 becomes equal to the maximum intensity (Pmax), as shown at a point B1 in FIGS. 4A and 4C. At a point B2 shown in FIGS. 4A and 4C, the output period of the pulse P1 reaches 100% of the first period T1. At this time, the integrated light amount S1 in the pulse P1 is given by Pmax/4×T1. The integrated light amount S2 in the pulse P2 is given by Pmax×3/4×T1. The sum of the integrated light amount S1 in the pulse P1 and the integrated light amount S2 in the pulse P2 is given by Pmax×T1.

A case in which after the output period of the pulse P1 reaches 100% of the first period T1 at the point B2 shown in FIGS. 4A and 4C and the sum of the intensity (Pmax/4) of the pulse P1 and the intensity (Pmax×3/4) of the pulse P2 becomes equal to the maximum intensity (Pmax), the light amount of the illumination light further increases at a point B3 or the like will be described next.

In this case, as shown in FIG. 4C, the integrated light amount S1 in the pulse P1 at the point B2 transits to the integrated light amount S2 in the pulse P2 in the first period T1 after the point B2 including the point B3. At the same time, the integrated light amount S2 in the pulse P2 transits to the integrated light amount S3 in the pulse P3. The pulse P3 indicates the light intensity in the second period T2, and the second period T2 continues from the first period T1, and is longer or shorter than the first period T1. The second period T2 may be equal to the first period T1. Transition indicates that the integrated light amount S1 in the pulse P1 as a transition source is firstly decreased by a predetermined amount, the integrated light amount S2 in the pulse P2 as a transition destination is secondly added with the predetermined amount, the integrated light amount S2 in the pulse P2 as a transition source is thirdly decreased by the predetermined amount, and the integrated light amount S3 in the pulse P3 as a transition destination is fourthly added with the predetermined amount. This predetermined amount is, for example, a transition amount, the difference between the above-described maximum and minimum integrated light amounts, and the maximum integrated light amount in the pulse P1 at the point B2, and is given by Pmax/4×T1. The predetermined amount decreasing and addition operations are performed at the same time. This means that the decreasing and addition operations are performed during one frame period Tf1. The illumination controller 100 performs such transition.

In this case, the integrated light amount S1 in the pulse P1 at the point B2 is given by Pmax/4×T1, the integrated light amount S2 in the pulse P2 at the point B2 is given by Pmax×3/4×T1, the integrated light amount S3 in the pulse P3 at the point B2 is 0, and the difference between the maximum and minimum integrated light amounts as the predetermined amount is given by Pmax/4×T1.

Although not shown, in a period after the point B2 including the point B3, firstly, since Pmax/4×T1 is decreased by Pmax/4×T1 as the predetermined amount (transition amount), the integrated light amount S1 in the pulse P1 as a transition source becomes 0. Although not shown, secondly, since Pmax/4×T1 as the predetermined amount (transition amount) is added to Pmax×3/4×T1, the integrated light amount S2 in the pulse P2 as a transition destination becomes Pmax×T1. As shown in FIG. 4C, thirdly, since Pmax×T1 is decreased by Pmax/4×T1 as the predetermined amount (transition amount), the integrated light amount S2 in the pulse P2 as a transition source becomes Pmax×3/4×T1. As shown in FIG. 4C, fourthly, the integrated light amount S3 in the pulse P3 as a transition destination is obtained by adding the predetermined amount (transition amount) to 0. Note that since the output period of the pulse P3 is the second period T2, the predetermined amount becomes Pmax/4×T1. That is, the integrated light amount S3 in the pulse P3 becomes Pmax/4×T1/T2. Since a transition operation from the pulse P2 to the pulse P3 is performed by the first and second operations, the illumination controller 100 controls the intensity of the pulse P2 and the intensity of the pulse P3 as continuous illumination so that the total sum of the integrated light amount S2 in the pulse P2 and the integrated light amount S3 in the pulse P3 becomes constant.

The illumination controller 100 sets the intensity of the pulse P2 to Pmax×3/4 so that the integrated light amount S2 in the pulse P2 becomes Pmax×3/4×T1. Furthermore, the illumination controller 100 sets the intensity of the pulse P3 to Pmax/4×T1/T2 so that the integrated light amount S3 in the pulse P3 becomes Pmax/4×T1. The intensity of the pulse P1 is kept at Pmax/4.

Next, in a period after the point B2 including the point B3, the intensity of the pulse P1 becomes Pmax/4. After that, if the light amount of the illumination light further increases in the period after the point B2 including the point B3, as shown in FIGS. 4A and 4C, the output period of the pulse P1 increases from 0% of the first period T1 to 100%.

Assume that, as shown at a point C2 (see FIGS. 4A and 4D), the output period of the pulse P1 becomes 100% of the first period T1 again. If the light amount of the illumination light further increases, the operations at the points B2 and B3 are repeated. Thus, the integrated light amount S3 in the pulse P3 becomes an amount obtained by adding a predetermined amount to Pmax/4×T1 as the original integrated light amount. The predetermined amount is the integrated light amount S1 in the pulse P1 at the point C2, and becomes Pmax/4×T1. Therefore, at a point C3, the integrated light amount S3 in the pulse P3 becomes Pmax×2/4×T1. The pulses P1 and P2 are the same as those at the points B2 and B3.

The illumination controller 100 sets the intensity of the pulse P3 to Pmax×2/4×T1/T2 so that the integrated light amount S3 in the pulse P3 becomes Pmax×2/4×T1. The intensity of the pulse P1 is kept at Pmax/4.

After the point C3 as well, every time the output period of the pulse P1 reaches 100% of the first period T1 again, the operations at the points C2 and C3 are repeated.

If the illumination controller 100 further increases the light amount (the integrated light amount S1 in the pulse P1) of the illumination light when the sum of the intensity of the pulse P1 and that of the pulse P2 is approximately (substantially) equal to the maximum intensity of the illumination light and the output period of the pulse P1 is maximum (that is, the integrated light amount S1 in the pulse P1 is the maximum integrated light amount), the illumination controller 100 performs the second increasing transition operation of decreasing the integrated light amount S2 in the pulse P2 as modulated illumination by the transition amount, and increasing the integrated light amount S3 in the pulse P3 as continuous illumination by the transition amount.

When causing the pulse P2 to transit to the pulse P3, the intensity of the pulse P3 necessary to achieve the integrated light amount in the pulse P3 after transition may exceed the maximum intensity Pmax. In this case, the illumination controller 100 adjusts the transition amount so the intensity of the pulse P3 does not exceed the maximum intensity Pmax. Alternatively, the illumination controller 100 may define the sum of the integrated light amounts before transition as the maximum light amount of the illumination light without causing the integrated light amount S2 in the pulse P2 to transit to the integrated light amount S3 in the pulse P3.

In the second period T2 at the time of transition to the pulse P3, a period (Tf1−Tr−Ta) from the end of exposure of the imager 61 to the start of exposure actually exists. Therefore, by replacing the second period T2 by T2−(Tf1−Tr−Ta), the imager 61 can actually perform an operation such as a light amount transition operation by a value corresponding to the exposure light amount.

A case in which when the light amount of the illumination light is controlled, the light amount control signal has information indicating that the light amount of the illumination light decreases with respect to the current state will be described below with reference to FIGS. 4A, 4E, and 4F.

Assume that the output period of the pulse P1 is set while the integrated light amounts S2 and S3 in the pulses P2 and P3 are maximum. The illumination controller 100 controls the intensity of the pulse P1 as an intensity of a constant value to 1/M (M is an integer of 2 or more) of the maximum intensity Pmax of the illumination light. The illumination controller 100 controls the intensity of the pulse P2 as an intensity of a constant value to (M−1)/M (M is an integer of 2 or more) of the maximum intensity Pmax of the illumination light. In this embodiment, $M=2^2=1$ is set. Note that the illumination controller 100 may form the pulse P1 by a plurality of pulses in the one frame period Tf1 or one field period. As described above, since the pulse P1 has a constant value, the integrated light amount S1 in the pulse P1 is controlled by adjusting the output period of the pulse P1. Adjustment and control are performed by the illumination controller 100. The output period corresponds to 0% to 100% of the first period T1. Since the light amount of the illumination light decreases with respect to the current state, the output period decreases.

A case in which the light amount of the illumination light further decreases at a point D1 or the like after the output period of the pulse P1 reaches 0% of the first period T1 in a period from a point D3 to a point D2 in FIGS. 4A and 4E (the integrated light amount S1 in the pulse P1 reaches the minimum integrated light amount) will be described.

Figure 4E:
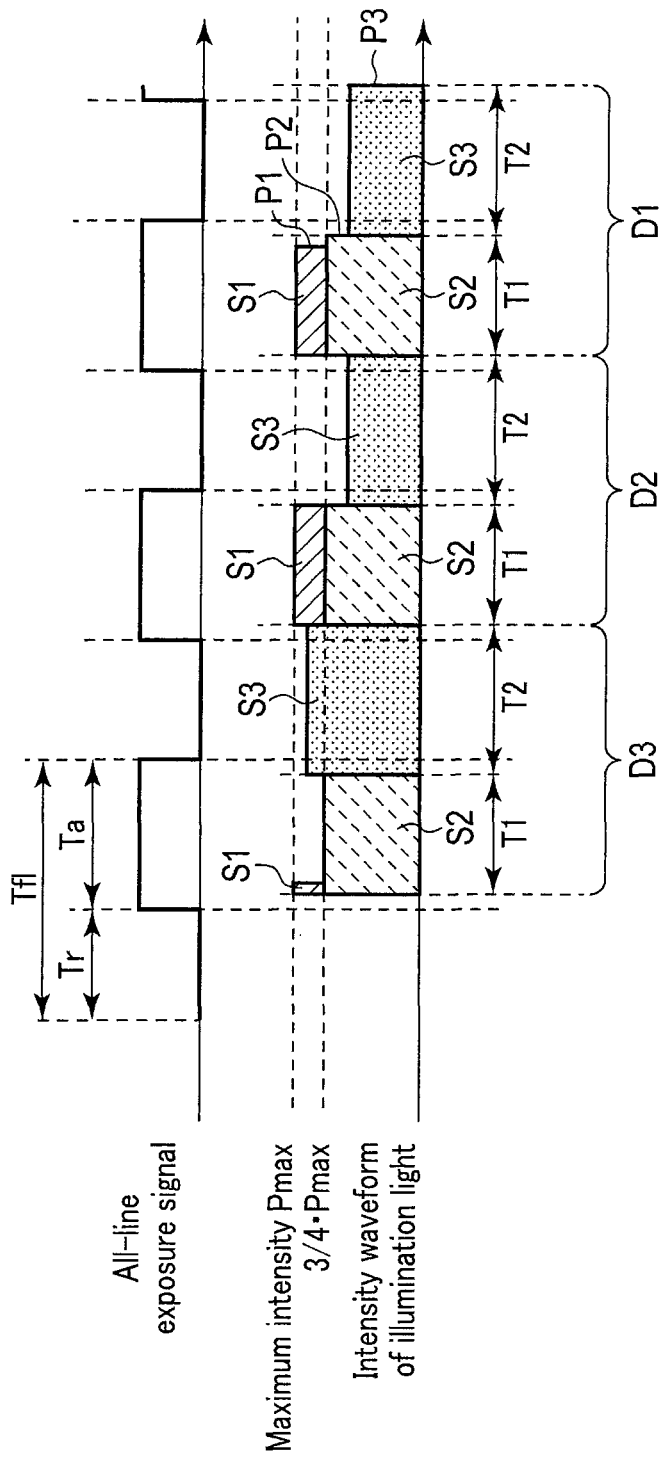
FIG. 4E is a timing chart, showing the relationship among the all-line exposure signal, the intensity waveform of the illumination light, and the integrated light amount at each of points D3, D2, and D1 shown in FIG. 4A, for explaining an example in which along with a decrease in light amount of the illumination light, the integrated light amount in the pulse P3 transits to the integrated light amount in the pulse P2 and the integrated light amount in the pulse P2 transits to the integrated light amount in the pulse P1.

In this case, as shown in FIG. 4E, the integrated light amount S3 in the pulse P3 at the point D2 transits to the integrated light amount S2 in the pulse P2 in the first period T1 after the point D2 including the point D3. At the same time, the integrated light amount S2 in the pulse P2 transits to the integrated light amount S1 in the pulse P1. Transition indicates that the integrated light amount S3 in the pulse P3 as a transition source is firstly decreased by a predetermined amount, the integrated light amount S2 in the pulse P2 as a transition destination is secondly added with the predetermined amount, the integrated light amount S2 in the pulse P2 as a transition source is thirdly decreased by the predetermined amount, and the integrated light amount S1 in the pulse P1 as a transition destination is fourthly added with the predetermined amount. The predetermined amount is, for example, a transition amount, the difference between the above-described maximum and minimum integrated light amounts, and the maximum integrated light amount in the pulse P1 at the point D2, and becomes Pmax/4×T1. The predetermined amount decreasing and addition operations are performed at the same time. The illumination controller 100 performs such transition.

In this case, at the point D3 shown in FIG. 4E, the integrated light amount S3 in the pulse P3 is given by Pmax×T1, and the integrated light amount S2 in the pulse P2 is given by Pmax×3/4×T1. The integrated light amount S1 in the pulse P1 is not 0 but a small value. The difference between the maximum and minimum integrated light amounts as the predetermined amount is given by Pmax/4×T1.

The illumination controller 100 sets the intensity of the pulse P2 to Pmax×3/4 so that the integrated light amount S2 in the pulse P2 becomes Pmax×3/4×T1. The illumination controller 100 sets the intensity of the pulse P3 to Pmax/4×T1/T2 so that the integrated light amount S3 in the pulse P3 becomes Pmax/4×T1. The intensity of the pulse P1 is kept at Pmax/4.

In a period after the point D2 including the point D1, firstly, the integrated light amount S3 in the pulse P3 as a transition source is obtained by decreasing Pmax×T1 by the predetermined amount (transition amount). The predetermined amount is given by Pmax/4×T1. Note that since the output period of the pulse P3 is the second period T2, the intensity of the pulse P3 is decreased by Pmax/4×T1/T2 before and after transition. That is, the intensity of the pulse P3 becomes Pmax×3/4×T1/T2. Although not shown, secondly, the integrated light amount S2 in the pulse P2 as a transition destination becomes Pmax×T1 since Pmax/4×T1 as the predetermined amount (transition amount) is added to Pmax×3/4×T1. As shown in FIG. 4E, thirdly, the integrated light amount S2 in the pulse P2 as a transition Source becomes Pmax×3/4×T1 since Pmax×T1 is decreased by Pmax/4×T1 as the predetermined amount (transition amount). As shown in FIG. 4E, fourthly, the integrated light amount S1 in the pulse P1 as a transition destination becomes Pmax/4×T1 since Pmax/4×T1 as the predetermined amount (transition amount) is added to 0. Thus, the output period of the pulse P1 returns to 100% of the first period T1. Since the first to fourth operations are simultaneously performed, the sum of the intensity of the pulse P1 and that of the pulse P2 never exceeds the maximum intensity Pmax. Since a transition operation from the pulse P2 to the pulse P3 is performed by the first and second operations, the illumination controller 100 controls the intensity of the pulse P2 and the intensity of the pulse P3 as continuous illumination so that the total sum of the integrated light amount S2 in the pulse P2 and the integrated light amount S3 in the pulse P3 is constant.

Note that at this time, the illumination controller 100 sets the intensity of the pulse P2 to Pmax×3/4 so that the integrated light amount S2 in the pulse P2 becomes Pmax×3/4 T1. The intensity of the pulse P1 is kept at Pmax/4.

As shown in FIGS. 4A and 4E, if the light amount of the illumination light further decreases in the period after the point D2 including the point D1, the output period of the pulse P1 decreases from 100% of the first period T1 to 0%.

Next, after the point D1 as well, every time the output period of the pulse P1 reaches 0% of the first period T1 again, the operations at the points D3 and D2 are repeated.

If the sum of the intensity of the pulse P1 and that of the pulse P2 is approximately (substantially) equal to the maximum intensity of the illumination light and the illumination controller 100 further decreases the light amount (the integrated light amount S1 in the pulse P1) of the illumination light, the illumination controller 100 performs the second decreasing transition operation of decreasing the integrated light amount S3 in the pulse P3 as continuous illumination by the transition amount, and increasing the integrated light amount S2 in the pulse P2 as modulated illumination by the transition amount.

Figure 4F:
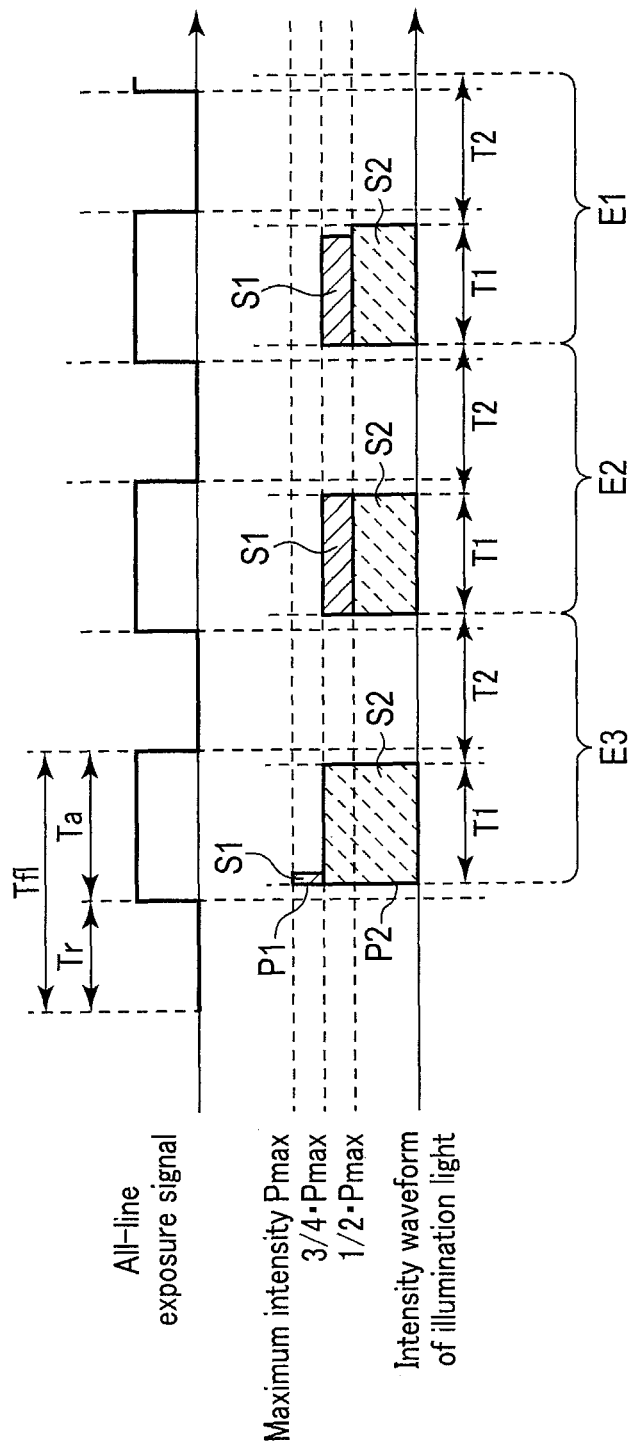
FIG. 4F is a timing chart, showing the relationship among the all-line exposure signal, the intensity waveform of the illumination light, and the integrated light amount at each of points E3, E2, and E1 shown in FIG. 4A, for explaining an example in which the integrated light amount in the pulse P2 transits to the integrated light amount in the pulse P1 along with a decrease in light amount of the illumination light.

If this operation is repeated, the integrated light amount S3 in the pulse P3 becomes 0, as shown in FIGS. 4A and 4F.

A case in which the light amount of the illumination light further decreases while the output period of the pulse P1 reaches 0% of the first period T1 will be described next.

In this case, as shown in FIG. 4F, the integrated light amount S2 in the pulse P2 at a point E3 transits to the integrated light amount S1 in the pulse P1 in the first period T1 after a point E2 including the point E3. Transition indicates that the integrated light amount S2 in the pulse P2 as a transition source is decreased by a predetermined amount, and the integrated light amount S1 in the pulse P1 as a transition destination is added with the predetermined amount. The predetermined amount is, for example, a transition amount, the difference between the above-described maximum and minimum integrated light amounts, and the maximum integrated light amount in the pulse P1 at the point E2, and becomes Pmax/4×T1. The predetermined amount decreasing and addition operations are performed at the same time. The illumination controller 100 performs such transition.

In this case, at the point E3 shown in FIG. 4F, the integrated light amount S2 in the pulse P2 is given by Pmax×3/4×T1. Although not shown, the integrated light amount S1 in the pulse P1 is 0. The difference between the maximum and minimum integrated light amounts as the predetermined amount is given by Pmax/4×T1.

In a period after the point E3 including the point E2, since Pmax×3/4×T1 is decreased by Pmax/4×T1 as the predetermined amount (transition amount), the integrated light amount S2 in the pulse P2 as a transition source becomes Pmax×2/4×T1. Since Pmax/4×T1 as the predetermined amount (transition amount) is added to 0, the integrated light amount S1 in the pulse P1 as a transition destination becomes Pmax/4×T1. Thus, the output period of the pulse P1 returns to 100% of the first period T1.

Next, as shown in FIGS. 4A and 4F, if the light amount of the illumination light further decreases in a period after a point E1 including the point E2, the output period of the pulse P1 decreases from 100% of the first period T1 to 0%.

After the point E1 as well, every time the output period of the pulse P1 reaches 0% of the first period T1 again, the operation at the point E2 is repeated.

If this operation is repeated, the integrated light amount S2 in the pulse P2 becomes 0 and the integrated light amount S1 in the pulse P1 also becomes 0 after a while.

As described above, if the illumination controller 100 further decreases the light amount of the illumination light in the one frame period Tf1 or one field period while the integrated light amount S1 in the pulse P1 is the minimum integrated light amount at the points E3 and E2, the illumination controller 100 performs the first decreasing transition operation of decreasing the integrated light amount S2 in the pulse P2 by the transition amount, and increasing the integrated light amount S1 in the pulse P1 by the transition amount. The illumination controller 100 sets the transition amount as the difference between the maximum and minimum integrated light amounts. At the point E1 after the first decreasing transition operation, the illumination controller 100 adjusts the output period of the pulse P1 so that the decrease amount of the light amount of the illumination light corresponds to the integrated light amount S1 in the pulse P1.

Figure 5A:
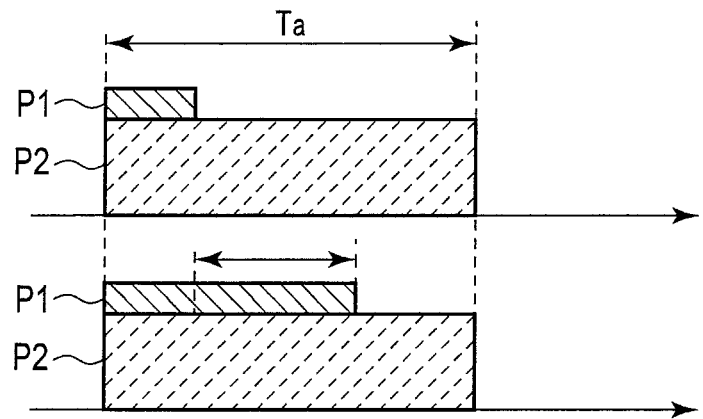
FIG. 5A is a timing chart showing an increase/decrease in output period of the pulse P1 according to the embodiment.
Figure 5B:
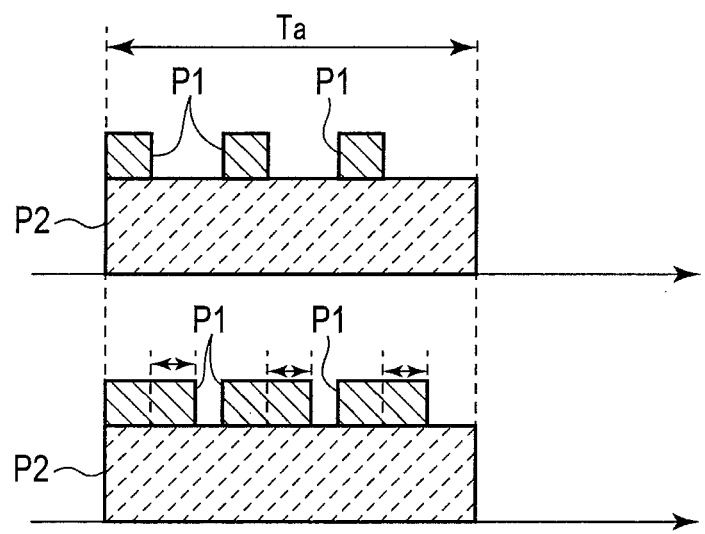
FIG. 5B is a timing chart showing an example of an increase/decrease in output period of the pulse P1, and showing PWM control.

In this embodiment, as shown in FIG. 5A, in one all-line exposure period Ta (non-reading period), the integrated light amount increases/decreases by increasing/decreasing the output period (pulse width) of the pulse P1. However, as shown in FIG. 5B, the plurality of pulses P1 may be arranged in one all-line exposure period Ta, and the output period of each pulse P1 may be adjusted, thereby adjusting the integrated light amount S1 (PWM control: Pulse Width Modulation control). As shown in FIG. 5C, the integrated light amount S1 may be adjusted by increasing/decreasing the number of pulses P1 (PNM control: Pulse Number Modulation control). As shown in FIG. 5D, the integrated light amount S1 may be adjusted by increasing/decreasing the density of the plurality of pulses P1 (the interval of the pulses P1) (PDM control: Pulse Density Modulation control). The integrated light amount may be adjusted by appropriately combining these techniques, as a matter of course. The illumination controller 100 may increase/decrease the output period of the pulse P1 by one of PWM control, PDM control, and PNM control. In this case, the illumination controller 100 sets the output period so that the total sum of the periods during which the pulses P1 are output corresponds to the output period. Furthermore, if components of the pulses P1 to be substantially applied to the light source 51 are limited in terms of the operation of the circuit, the illumination controller 100 sets, as an output period, a period corresponding to the total sum of the components to be substantially applied.

In this embodiment, in a state in which the all-line exposure period Ta and the reading period Tr are mixed, the light amount of the illumination light is controlled by the pulses P1, P2, and P3 while keeping the pulse P3 constant in continuous illumination. In this embodiment, when the imager 61 performs exposure for each horizontal line, it is possible to suppress occurrence of bright and dark fringes in an image, thereby widening the dynamic range of light control. In this embodiment, it is possible to make the most of the capability of the light source 51 by the pulse P3.

If the integrated light amount S3 in the pulse P3 suddenly changes, exposure light amounts for respective lines are largely different due to overlapping of the exposure periods of consecutive preceding and succeeding frames, causing bright and dark fringes in the image. However, in this embodiment, by decreasing the step amount of an increase/decrease in integrated light amount S3 in the pulse P3 to a fraction of the maximum intensity of the illumination light, it is possible to suppress occurrence of bright and dark fringes in the image caused by overlapping of consecutive preceding and succeeding frames.

[First Modification]

First modification of the first embodiment will be described below with reference to FIGS. 6A and 6B. The same reference numerals as in the first embodiment denote the same portions and a detailed description thereof will be omitted.

In the first embodiment, if the light amount of the illumination light increases and the second increasing transition operation is performed, the timing of transiting from the integrated light amount S2 in the pulse P2 to the integrated light amount S3 in the pulse P3 coincides with the timing of transiting from the integrated light amount S1 in the pulse P1 to the integrated light amount S2 in the pulse P2, and transition is performed in the one frame period Tf1.

Figure 6A:
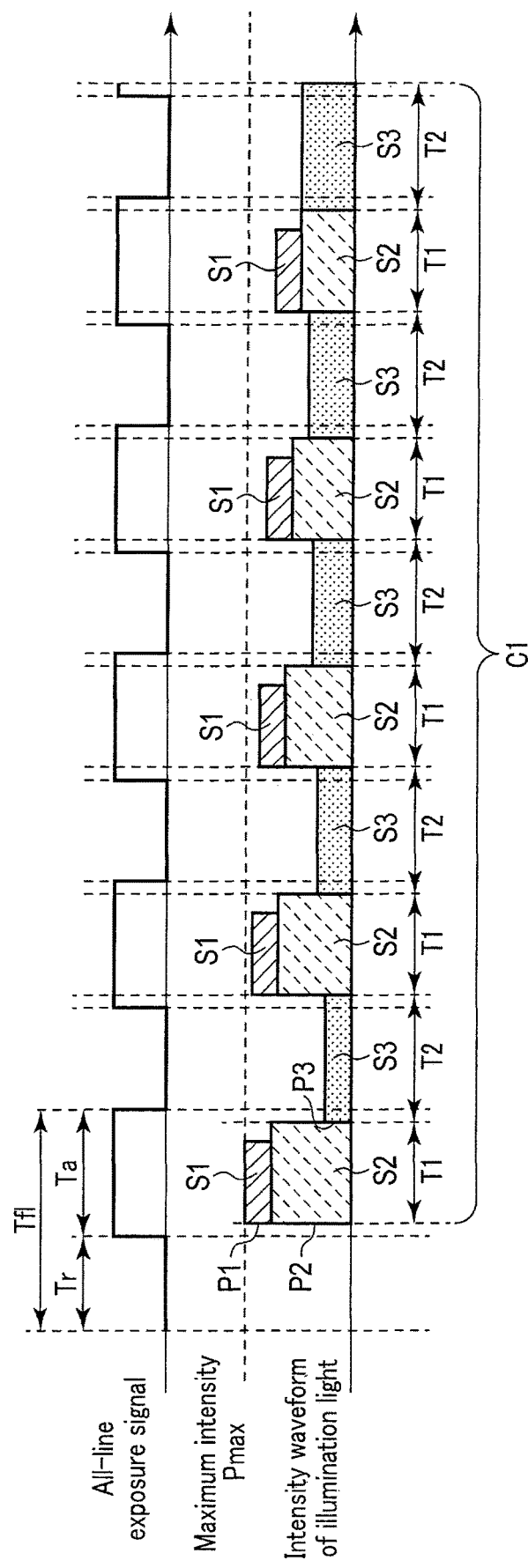
FIG. 6A is a timing chart, showing first modification of the first embodiment, for explaining an example in which if the light amount of the illumination light increases at the point C1 shown in FIG. 4A, the integrated light amount in the pulse P2 transits to the integrated light amount in the pulse P3 before the integrated light amount in the pulse P1 transits to the integrated light amount in the pulse P2, and transition is performed in a plurality of frame periods.

However, in this modification, as shown in FIG. 6A, before transiting from the integrated light amount S1 in the pulse P1 to the integrated light amount S2 in the pulse P2, transition from the integrated light amount S2 in the pulse P2 to the integrated light amount S3 in the pulse P3 is performed, and transition is performed in a plurality of frame periods Tf1.

In the first embodiment, if the light amount of the illumination light decreases and the second decreasing transition operation is performed, the timing of transiting from the integrated light amount S3 in the pulse P3 to the integrated light amount S2 in the pulse P2 coincides with the timing of transiting from the integrated light amount S2 in the pulse P2 to the integrated light amount S1 in the pulse P1, and transition is performed in the one frame period Tf1.

Figure 6B:
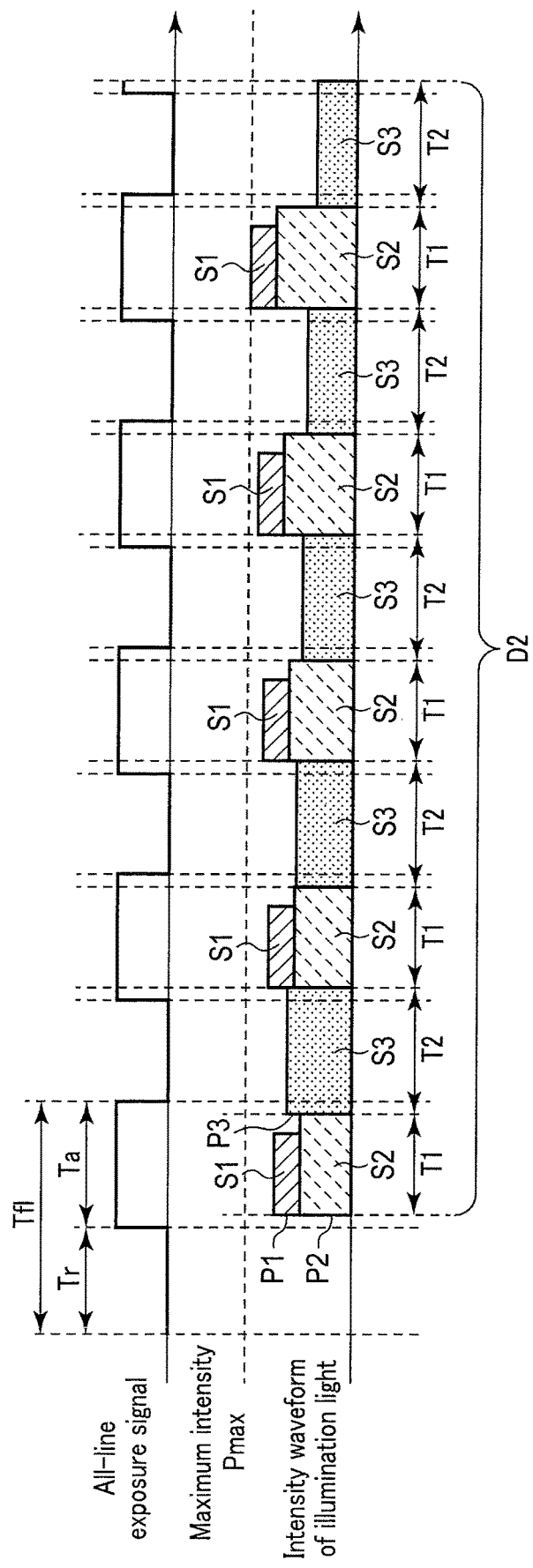
FIG. 6B is a timing chart, showing first modification of the first embodiment, for explaining an example in which if the light amount of the illumination light decreases, the integrated light amount in the pulse P3 transits to the integrated light amount in the pulse P2 before the integrated light amount in the pulse P2 transits to the integrated light amount in the pulse P1, and transition is performed in a plurality of the frame periods Tf1.

However, in this modification, as shown in FIG. 6B, before transiting from the integrated light amount S2 in the pulse P2 to the integrated light amount S1 in the pulse P1, transition from the integrated light amount S3 in the pulse P3 to the integrated light amount S2 in the pulse P2 is performed, and transition is performed in a plurality of frame periods Tf1.

As described above, at least one of the second increasing transition operation and the second decreasing transition operation is performed in a plurality of frame periods or a plurality of field periods after the start of transition.

Transition from the integrated light amount S3 in the pulse P3 to the integrated light amount S2 in the pulse P2 and transition from the integrated light amount S2 in the pulse P2 to the integrated light amount S3 in the pulse P3 may be performed simultaneously with an increase/decrease in integrated light amount S1 in the pulse P1.

In this modification, the exposure light amounts for respective lines are largely different due to overlapping of the exposure periods of consecutive preceding and succeeding frames. In this modification, this difference can be reduced when the integrated light amount S3 in the pulse P3 gradually increases/decreases, thereby suppressing occurrence of bright and dark fringes in an image.

[Second Modification]

Figure 7:
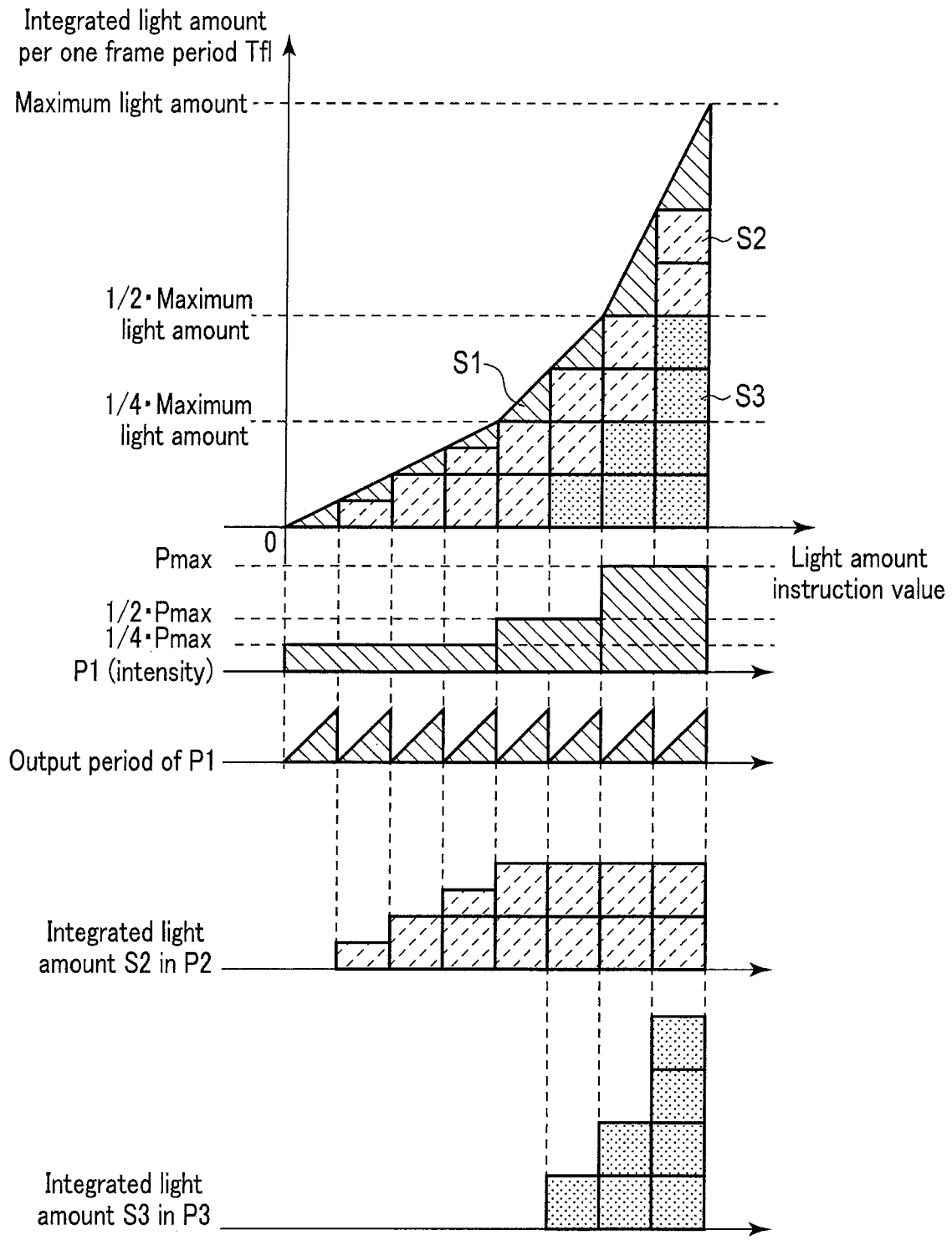
FIG. 7 shows graphs showing second modification of the first embodiment and showing the relationship among the integrated light amount per one frame period, the pulse P1, the integrated light amount in the pulse P1, the integrated light amount in a pulse P2, and the integrated light amount in a pulse P3.

Second modification of the first embodiment will be described below with reference to FIG. 7. The same reference numerals as in the first embodiment denote the same portions and a detailed description thereof will be omitted.

In the first embodiment, the intensity of the pulse P1 is 1/M (M is an integer of 2 or more) of the maximum intensity Pmax of the illumination light, and has a constant value.

However, in this modification, the pulse P1 changes in accordance with the light amount of the illumination light.

For example, if the light amount of the illumination light is small, the illumination controller 100 controls the intensity of the pulse P1 to be lower than 1/M (M is an integer of 2 or more) of the maximum intensity Pmax of the illumination light. For example, if the light amount of the illumination light is equal to or smaller than ¼ of the maximum light amount, the illumination controller 100 controls the intensity of the pulse P1 to ½ of 1/M (M is an integer of 2 or more) of the maximum intensity Pmax of the illumination light.

Furthermore, in this modification, if the light amount of the illumination light is large, the illumination controller 100 controls the intensity of the pulse P1 to be higher than 1/M (M is an integer of 2 or more) of the maximum intensity Pmax of the illumination light. For example, if the light amount of the illumination light is equal to or larger than ½ of the maximum light amount, the illumination controller 100 controls the intensity of the pulse P1 to be twice 1/M (M is an integer of 2 or more) of the maximum intensity Pmax of the illumination light.

In this modification, if the light amount of the illumination light is small, the resolving power to an increase/decrease in light amount can be increased, thereby improving a resolving power in light control.

At this time, the maximum light amount (maximum integrated light amount) may be given by Pmax×T1×2 or Pmax×(T1+T2). The present invention is not limited to each embodiment described above, and constituent elements can be modified and embodied in the execution stage within the spirit and scope of the invention. In addition, various inventions can be formed by proper combinations of a plurality of constituent elements disclosed in the above embodiments.

What is claimed is:

1. An imaging system comprising:
   an illumination portion configured to emit illumination light with which a main target is illuminated;
   an imager including pixels two-dimensionally arrayed and each configured to generate an electrical signal by photoelectrically converting received light;
   a reader having a reading period during which part of lines of the pixels are read in one of one frame period and one field period and configured to sequentially read the electrical signals generated by the pixels for each line of the pixels; and
   an illumination controller configured to control an intensity of the illumination light based on modulated illumination for modulating the intensity of the illumination light in a non-reading period as a period other than the reading period,
   wherein in the non-reading period, the modulated illumination has a first integrated light amount as a product of a variable intensity of a first pulse and an output period of the illumination light and a second integrated light amount as a product of a constant intensity of a second pulse and the output period,
   wherein in the non-reading period, the illumination controller causes a predetermined light amount that is not larger than a maximum value of the first integrated light amount and is not smaller than a minimum value of the second integrated light amount to transit between the first integrated light amount and the second integrated light amount,
wherein as the illumination controller increases a light amount of the illumination light in one of the one frame period and the one field period in a state in which the first integrated light amount is a maximum integrated light amount, the illumination controller performs a first increasing transition operation of decreasing the first integrated light amount by a predetermined transition amount and increasing the second integrated light amount by the predetermined transition amount, and
wherein the illumination controller adjusts the output period of the first pulse after the first increasing transition operation so that an increased amount of the light amount of the illumination light corresponds to the first integrated light amount.

2. The imaging system of claim 1, wherein the illumination controller controls the intensity of the illumination light based on the modulated illumination and continuous illumination that is performed in part of the reading period to keep the intensity of the illumination light constant, and wherein the illumination controller causes the predetermined light amount to transit between the first integrated light amount and the second integrated light amount, and then causes a predetermined light amount that is not larger than the maximum value of the first integrated light amount and is not smaller than a minimum value of a third integrated light amount in a third pulse included in the continuous illumination to transit between the first integrated light amount and the third integrated light amount.

3. The imaging system of claim 2, wherein the maximum integrated light amount comprises a product of the intensity of the first pulse and a maximum value of the output period, and wherein the minimum integrated light amount comprises a product of the intensity of the first pulse and a minimum value of the output period, and wherein the illumination controller increases/decreases the first integrated light amount between the maximum integrated light amount and the minimum integrated light amount by increasing/decreasing the output period, thereby increasing/decreasing the light amount of the illumination light.

4. The imaging system of claim 1, wherein if the illumination controller further decreases the light amount of the illumination light in one of the one frame period and the one field period in a state in which the first integrated light amount is the minimum integrated light amount, the illumination controller performs a first decreasing transition operation of decreasing the second integrated light amount by the predetermined transition amount and increasing the first integrated light amount by the transition amount, and wherein after the first decreasing transition operation, the illumination controller adjusts the output period of the first pulse so that a decrease amount of the light amount of the illumination light corresponds to the first integrated light amount.

5. The imaging system of claim 1, wherein the illumination controller sets the transition amount as a difference between the maximum integrated light amount and a minimum integrated light amount.

6. The imaging system of claim 5, wherein the illumination controller controls the intensity of the first pulse to 1/M (wherein M is an integer not smaller than 2) of a maximum intensity of the illumination light.

7. The imaging system of claim 5, wherein if a sum of the intensity of the first pulse and the intensity of the second pulse is approximately equal to the maximum intensity of the illumination light, and the illumination controller further increases the light amount of the illumination light, the illumination controller performs a second increasing transition operation of decreasing the second integrated light amount by the transition amount and increasing an integrated light amount in the continuous illumination by the transition amount, and wherein if the sum of the intensity of the first pulse and the intensity of the second pulse is approximately equal to the maximum intensity of the illumination light, and the illumination controller further decreases the first integrated light amount, the illumination controller performs a second decreasing transition operation of decreasing an integrated light amount in the continuous illumination by the transition amount and increasing the second integrated light amount by the transition amount.

8. The imaging system of claim 7, wherein at least one of the second increasing transition operation and the second decreasing transition operation is performed in a plurality of frame periods or a plurality of field periods after a start of transition.

9. The imaging system of claim 1, wherein the illumination controller controls the intensity of the second pulse and the intensity in the continuous illumination so that a total sum of the second integrated light amount and an integrated light amount in the continuous illumination is constant.

10. The imaging system of claim 1, wherein the illumination controller increases/decreases the output period of the first pulse by one of PWM control, PDM control, and PNM control.

11. The imaging system of claim 1, further comprising an image processor configured to generate an image of the main target by image processing for the electrical signals output from the pixels,
wherein the image processor includes a detector configured to detect a luminance value of the main target included in the image, and
wherein the illumination controller controls an increase/decrease in the light amount of the illumination light based on the luminance value detected by the detector.

12. The imaging system of claim 1, further comprising an illumination device comprising:
a light source configured to emit primary light,
a light guide configured to guide the primary light emitted from the light source, and
an optical converter of the illumination portion, configured to convert the primary light guided by the light guide into secondary light having optical characteristics different from those of the primary light.

13. An endoscope system comprising an imaging system according to claim 1 and including an endoscope and a light source device from which the endoscope is detachable.

14. An imaging system comprising:
an illumination portion configured to emit illumination light with which a main target is illuminated;
an imager including pixels two-dimensionally arrayed and each configured to generate an electrical signal by photoelectrically converting received light;
a reader having a reading period during which part of lines of the pixels are read in one of one frame period and one field period and configured to sequentially read the electrical signals generated by the pixels for each line of the pixels; and
an illumination controller configured to control an intensity of the illumination light based on modulated illumination for modulating the intensity of the illumination light in a non-reading period as a period other than the reading period, wherein in the non-reading period, the modulated illumination has a first integrated light amount as a product of a variable intensity of a first pulse and an output period of the illumination light and a second integrated light amount as a product of a constant intensity of a second pulse and the output period, wherein in the non-reading period, the illumination controller causes a predetermined light amount that is not larger than a maximum value of the first integrated light amount and is not smaller than a minimum value of the second integrated light amount to transit between the first integrated light amount and the second integrated light amount, wherein as the illumination controller decreases a light amount of the illumination light in one of the one frame period and the one field period in a state in which the first integrated light amount is a minimum integrated light amount, the illumination controller performs a first decreasing transition operation of decreasing the second integrated light amount by a predetermined transition amount and increasing the first integrated light amount by the predetermined transition amount, and wherein the illumination controller adjusts the output period of the first pulse after the first decreasing transition operation so that a decreased amount of the light amount of the illumination light corresponds to the first integrated light amount.

15. The imaging system of claim 14, wherein the illumination controller controls the intensity of the illumination light based on the modulated illumination and continuous illumination that is performed in part of the reading period to keep the intensity of the illumination light constant, and wherein the illumination controller causes the predetermined light amount to transit between the first integrated light amount and the second integrated light amount, and then causes a predetermined light amount that is not larger than the maximum value of the first integrated light amount and is not smaller than a minimum value of a third integrated light amount in a third pulse included in the continuous illumination to transit between the first integrated light amount and the third integrated light amount.

16. The imaging system of claim 15, wherein the maximum integrated light amount comprises a product of the intensity of the first pulse and a maximum value of the output period, and wherein the minimum integrated light amount comprises a product of the intensity of the first pulse and a minimum value of the output period, and wherein the illumination controller increases/decreases the first integrated light amount between the maximum integrated light amount and the minimum integrated light amount by increasing/decreasing the output period, thereby increasing/decreasing the light amount of the illumination light.

17. The imaging system according to of claim 14, wherein the illumination controller sets the transition amount as a difference between the maximum integrated light amount and the minimum integrated light amount.

18. The imaging system according to of claim 5, wherein if a sum of the intensity of the first pulse and the intensity of the second pulse is approximately equal to the maximum intensity of the illumination light, and the illumination controller further increases the light amount of the illumination light, the illumination controller performs a second increasing transition operation of decreasing the second integrated light amount by the transition amount and increasing an integrated light amount in the continuous illumination by the transition amount, and wherein if the sum of the intensity of the first pulse and the intensity of the second pulse is approximately equal to the maximum intensity of the illumination light, and the illumination controller further decreases the first integrated light amount, the illumination controller performs a second decreasing transition operation of decreasing an integrated light amount in the continuous illumination by the transition amount and increasing the second integrated light amount by the transition amount.

19. The imaging system according to of claim 18, wherein at least one of the second increasing transition operation and the second decreasing transition operation is performed in a plurality of frame periods or a plurality of field periods after a start of transition.

20. The imaging system according to of claim 15, wherein the illumination controller controls the intensity of the second pulse and the intensity in the continuous illumination so that a total sum of the second integrated light amount and an integrated light amount in the continuous illumination is constant.

* * * * *